United States Patent
Naruse et al.

(10) Patent No.: US 11,278,655 B2
(45) Date of Patent: Mar. 22, 2022

(54) BLOOD PURIFICATION APPARATUS

(71) Applicant: Nikkiso Company Limited, Tokyo (JP)

(72) Inventors: Yuta Naruse, Shizuoka (JP); Shinya Hasegawa, Shizuoka (JP); Wataru Matsushita, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 510 days.

(21) Appl. No.: 16/037,170

(22) Filed: Jul. 17, 2018

(65) Prior Publication Data
US 2018/0318490 A1 Nov. 8, 2018

Related U.S. Application Data

(63) Continuation of application No. PCT/JP2017/002570, filed on Jan. 25, 2017.

(30) Foreign Application Priority Data

Jan. 25, 2016 (JP) .............................. JP2016-011815

(51) Int. Cl.
*A61M 1/36* (2006.01)
*B01D 61/32* (2006.01)
(Continued)

(52) U.S. Cl.
CPC ............ *A61M 1/3639* (2013.01); *A61M 1/14* (2013.01); *A61M 1/36* (2013.01); *A61M 1/3607* (2014.02);
(Continued)

(58) Field of Classification Search
CPC ................................................ A61M 1/3621
See application file for complete search history.

(56) References Cited

U.S. PATENT DOCUMENTS

| 4,493,693 A | 1/1985 | Bilstad et al. |
| 5,336,051 A | 8/1994 | Tamari |

(Continued)

FOREIGN PATENT DOCUMENTS

| EP | 0330891 A1 | 9/1989 |
| EP | 2361643 A1 | 8/2011 |

(Continued)

OTHER PUBLICATIONS

International Search Report from the Japanese Patent Office for Application No. PCT/JP2017/002570 dated Feb. 28, 2017.

(Continued)

*Primary Examiner* — Catharine L Anderson
*Assistant Examiner* — Arjuna P Chatrathi
(74) *Attorney, Agent, or Firm* — Young Basile Hanlon & MacFarlane, P.C.

(57) ABSTRACT

A blood purification apparatus in which whether or not the connection of a communicating line is appropriate can be determined more accurately. A blood purification apparatus includes a control device that is capable of executing a pressure-applying step in which a negative pressure or a positive pressure is applied to a flow route of one of a tube section and a blood circuit; a propagating step in which the negative pressure or the positive pressure applied in the pressure-applying step is propagated to the flow route of an other of the tube section and the blood circuit through the communicating line; and a checking step in which whether or not the propagation of the negative pressure or the positive pressure in the propagating step is successful is checked with reference to the pressure detected by the pressure-detecting device, and in which whether or not the connection of the communicating line is appropriate is checked with reference to whether or not the propagation of the negative pressure or the positive pressure is successful.

20 Claims, 20 Drawing Sheets

(51) Int. Cl.
*A61M 1/14* (2006.01)
*A61M 39/28* (2006.01)

(52) U.S. Cl.
CPC ........ *A61M 1/3644* (2014.02); *A61M 1/3649* (2014.02); *A61M 39/28* (2013.01); *B01D 61/32* (2013.01); *A61M 2205/3331* (2013.01); *A61M 2205/3337* (2013.01)

(56) References Cited

U.S. PATENT DOCUMENTS

| | | | |
|---|---|---|---|
| 5,920,054 A | 7/1999 | Uber | |
| 5,927,951 A | 7/1999 | Tamari | |
| 6,044,691 A * | 4/2000 | Kenley | A61M 1/3639 |
| | | | 73/40.5 R |
| 6,374,084 B1 | 4/2002 | Fok | |
| 6,497,680 B1 | 12/2002 | Holst | |
| 6,533,747 B1 * | 3/2003 | Polaschegg | A61M 1/3663 |
| | | | 604/6.09 |
| 6,868,720 B2 | 3/2005 | Lobdell | |
| 7,147,616 B2 | 12/2006 | Pedrazzi et al. | |
| 8,011,905 B2 | 9/2011 | Artsyukhovich | |
| 8,092,414 B2 | 1/2012 | Schnell et al. | |
| 8,608,680 B2 * | 12/2013 | Hasegawa | A61M 1/342 |
| | | | 604/6.11 |
| 8,900,173 B2 * | 12/2014 | Sugioka | A61M 1/342 |
| | | | 604/6.09 |
| 8,960,010 B1 | 2/2015 | Crnkovich et al. | |
| 9,192,708 B2 | 11/2015 | Iwahori et al. | |
| 9,662,433 B2 | 5/2017 | Matsuo | |
| 2003/0115965 A1 | 6/2003 | Mittelstein et al. | |
| 2006/0079826 A1 | 4/2006 | Beden et al. | |
| 2009/0024070 A1 | 1/2009 | Gelfand et al. | |
| 2009/0043240 A1 | 2/2009 | Robinson et al. | |
| 2009/0312686 A1 | 12/2009 | Sakamoto et al. | |
| 2010/0168640 A1 | 7/2010 | Kopperschmidt et al. | |
| 2010/0234787 A1 * | 9/2010 | Masaoka | A61M 1/1617 |
| | | | 604/5.04 |
| 2010/0274172 A1 | 10/2010 | Guenther et al. | |
| 2011/0139690 A1 | 6/2011 | Akita et al. | |
| 2011/0213289 A1 | 9/2011 | Toyoda | |
| 2012/0000547 A1 | 1/2012 | Gronau et al. | |
| 2013/0035626 A1 | 2/2013 | Suzuki | |
| 2013/0150766 A1 | 6/2013 | Gambro | |
| 2013/0150768 A1 * | 6/2013 | Sakamoto | A61M 1/3644 |
| | | | 604/6.09 |
| 2013/0172803 A1 | 7/2013 | Gambro | |
| 2013/0292313 A1 | 11/2013 | Fava et al. | |
| 2014/0138301 A1 | 5/2014 | Iwahori et al. | |
| 2014/0219829 A1 | 8/2014 | Matsuo et al. | |
| 2015/0021244 A1 | 1/2015 | Furuhashi et al. | |
| 2015/0150136 A1 | 6/2015 | Furuhashi et al. | |
| 2015/0238677 A1 | 8/2015 | Akita et al. | |
| 2016/0250405 A1 | 9/2016 | Kogoshi et al. | |
| 2017/0095602 A1 | 4/2017 | Ishizaki et al. | |
| 2017/0173249 A1 | 6/2017 | Matshushita et al. | |
| 2017/0312412 A1 | 11/2017 | Mochizuki et al. | |
| 2018/0071449 A1 | 3/2018 | Hasegawa et al. | |
| 2018/0080843 A1 | 3/2018 | Funamura et al. | |
| 2018/0140766 A1 | 5/2018 | Mochizuki et al. | |

FOREIGN PATENT DOCUMENTS

| | | |
|---|---|---|
| EP | 2535067 A1 | 12/2012 |
| EP | 2883558 A1 | 6/2015 |
| JP | S60-153138 U | 10/1985 |
| JP | S64-022357 U | 2/1989 |
| JP | H01-201263 A | 8/1989 |
| JP | H03-001290 | 1/1991 |
| JP | H03-073162 A | 3/1991 |
| JP | H06-047090 B2 | 2/1994 |
| JP | H08-510812 A | 11/1996 |
| JP | 2002-113096 A | 4/2002 |
| JP | 2003-093501 A | 4/2003 |
| JP | 2003-093503 A | 4/2003 |
| JP | 2003-519539 A | 6/2003 |
| JP | 2003-265301 A | 9/2003 |
| JP | 2003-290342 A | 10/2003 |
| JP | 2004-016619 A | 1/2004 |
| JP | 2004-049494 A | 2/2004 |
| JP | 2004-187990 A | 7/2004 |
| JP | 2004-313522 A | 11/2004 |
| JP | 2005-253555 A | 9/2005 |
| JP | 2006-280775 A | 10/2006 |
| JP | 2007-007435 A | 1/2007 |
| JP | 3128724 U | 1/2007 |
| JP | 2007-020962 A | 2/2007 |
| JP | 2007-135885 A | 6/2007 |
| JP | 2007-167108 A | 7/2007 |
| JP | 2007-282737 A | 11/2007 |
| JP | 2008-289635 A | 12/2008 |
| JP | 2009-112651 A | 5/2009 |
| JP | 2009-131412 A | 6/2009 |
| JP | 2009-525770 A | 7/2009 |
| JP | 2009-207706 A | 9/2009 |
| JP | 2010-273784 A | 12/2009 |
| JP | 2010-000161 A | 1/2010 |
| JP | 2010-136841 A | 6/2010 |
| JP | 2010-184029 A | 8/2010 |
| JP | 2010-188170 A | 9/2010 |
| JP | 2010-273693 A | 12/2010 |
| JP | 2011-030880 A | 2/2011 |
| JP | 2011-161060 A | 8/2011 |
| JP | 2012-034782 A | 2/2012 |
| JP | 2012-095842 A | 5/2012 |
| JP | 2012-095843 A | 5/2012 |
| JP | 2012-139405 A | 7/2012 |
| JP | 2012-192099 A | 10/2012 |
| JP | 2012-192100 A | 10/2012 |
| JP | 2012-192101 A | 10/2012 |
| JP | 2012-200340 A | 10/2012 |
| JP | 2013-027494 A | 2/2013 |
| JP | 2013-027495 A | 2/2013 |
| JP | 2013-056079 A | 3/2013 |
| JP | 2014-097197 A | 5/2014 |
| JP | 2014-184108 A | 10/2014 |
| JP | 5699008 B2 | 4/2015 |
| WO | 94/28309 A1 | 12/1994 |
| WO | 2001/051106 A1 | 7/2001 |
| WO | 2004/000391 A1 | 12/2003 |
| WO | 2005/118485 A1 | 12/2005 |
| WO | 2007/093064 A1 | 8/2007 |
| WO | 2009/004777 A1 | 1/2009 |
| WO | 2009/064741 A1 | 5/2009 |
| WO | 2009/074588 A1 | 6/2009 |
| WO | 2010/020390 A1 | 2/2010 |
| WO | 2011/099521 A1 | 8/2011 |
| WO | 2012/017959 A1 | 2/2012 |
| WO | 2013/031965 A1 | 3/2013 |
| WO | 2013/151114 A1 | 10/2013 |
| WO | 2014/024972 A1 | 2/2014 |
| WO | 2014/107656 A1 | 7/2014 |
| WO | 2015/068833 A1 | 5/2015 |

OTHER PUBLICATIONS

Co-pending U.S. Appl. No. 15/387,913 published as USS2017/0095602A1 dated Dec. 22, 2016.
Co-pending U.S. Appl. No. 15/819,219 published as US2018/0071449A1 dated Nov. 21, 2017.
Co-pending U.S. Appl. No. 15/823,794 published as US2018/0080843A1 dated Nov. 28, 2017.
Co-pending U.S. Appl. No. 15/874,023 published as US2018/0140766A1, filed Jan. 18, 2018.
Co-pending U.S. Appl. No. 15/952,419, filed Apr. 13, 2018.

* cited by examiner

[Fig. 1]
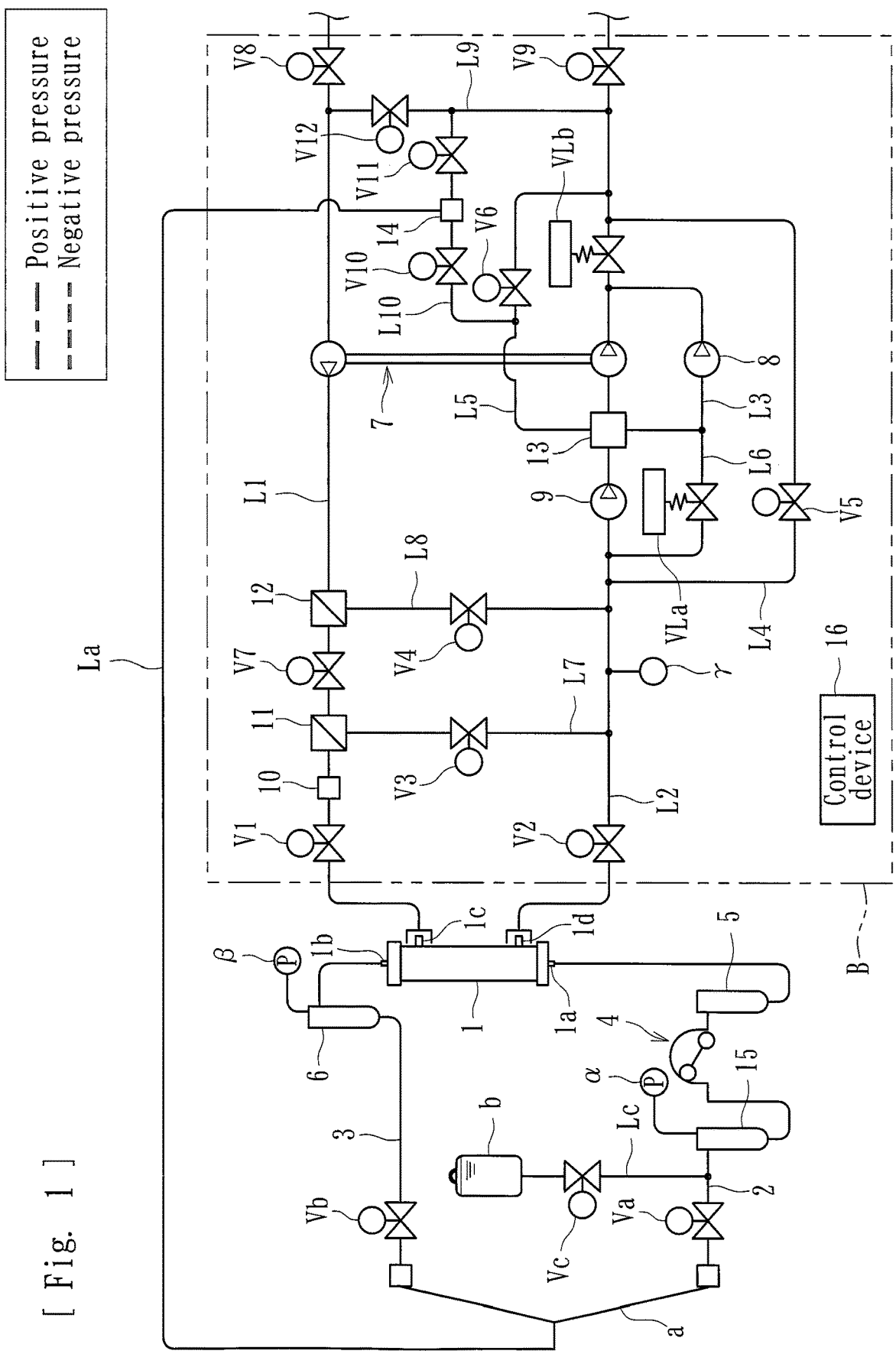

[Fig. 2]

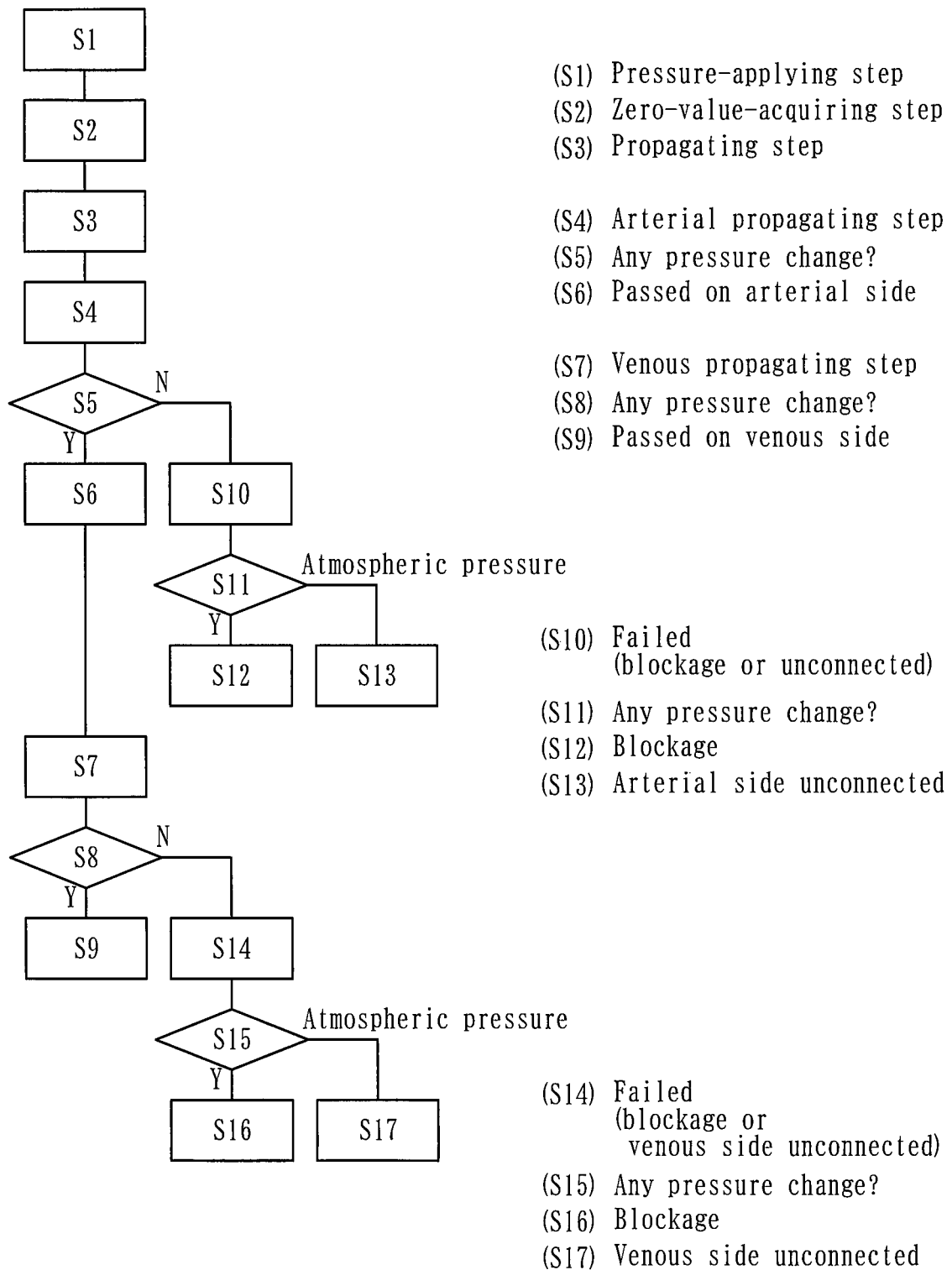

(S1) Pressure-applying step
(S2) Zero-value-acquiring step
(S3) Propagating step (S4) Arterial propagating step
(S5) Any pressure change?
(S6) Passed on arterial side (S7) Venous propagating step
(S8) Any pressure change?
(S9) Passed on venous side (S10) Failed (blockage or unconnected)
(S11) Any pressure change?
(S12) Blockage
(S13) Arterial side unconnected (S14) Failed (blockage or venous side unconnected)
(S15) Any pressure change?
(S16) Blockage
(S17) Venous side unconnected

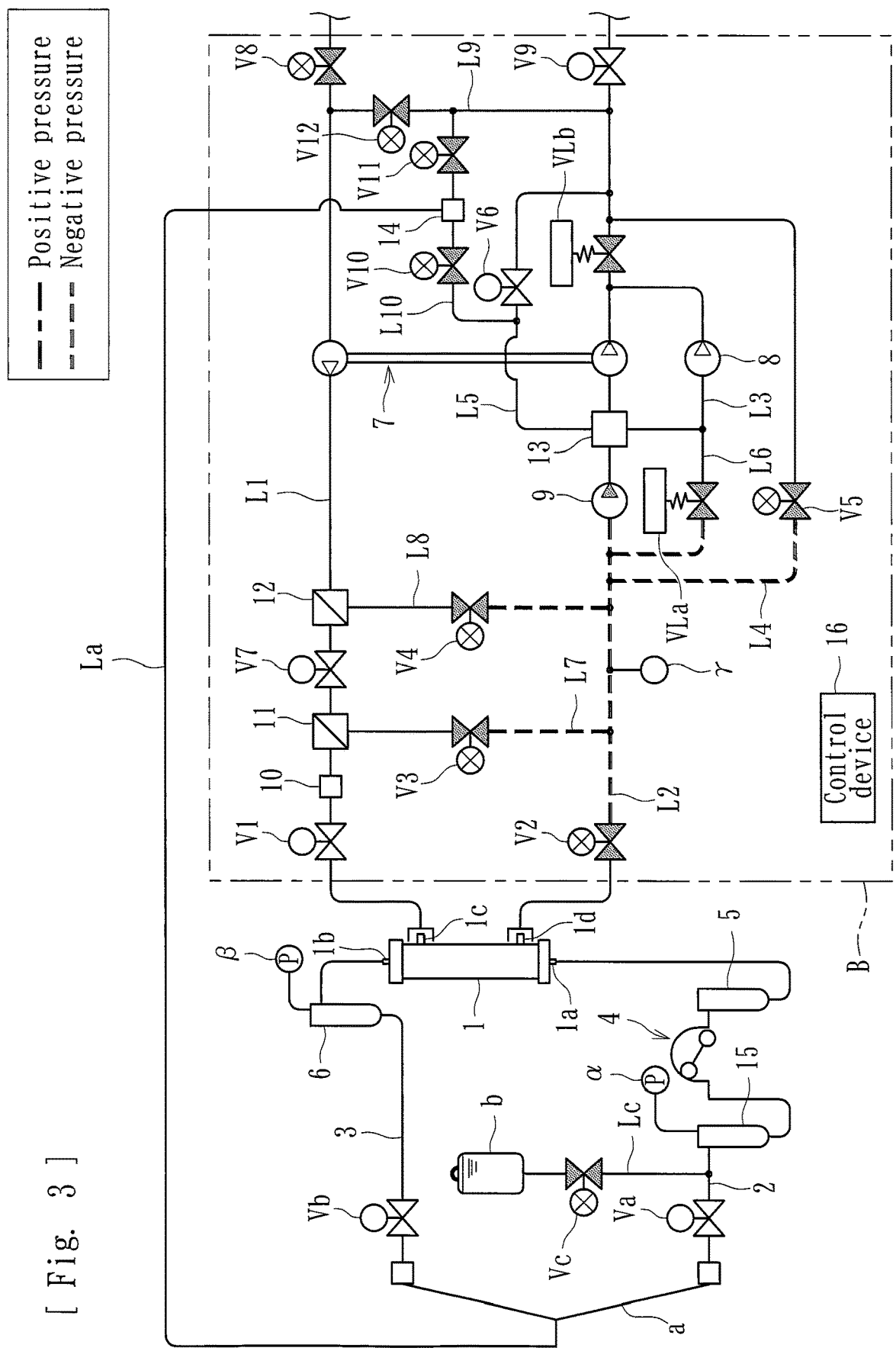
[Fig. 3]

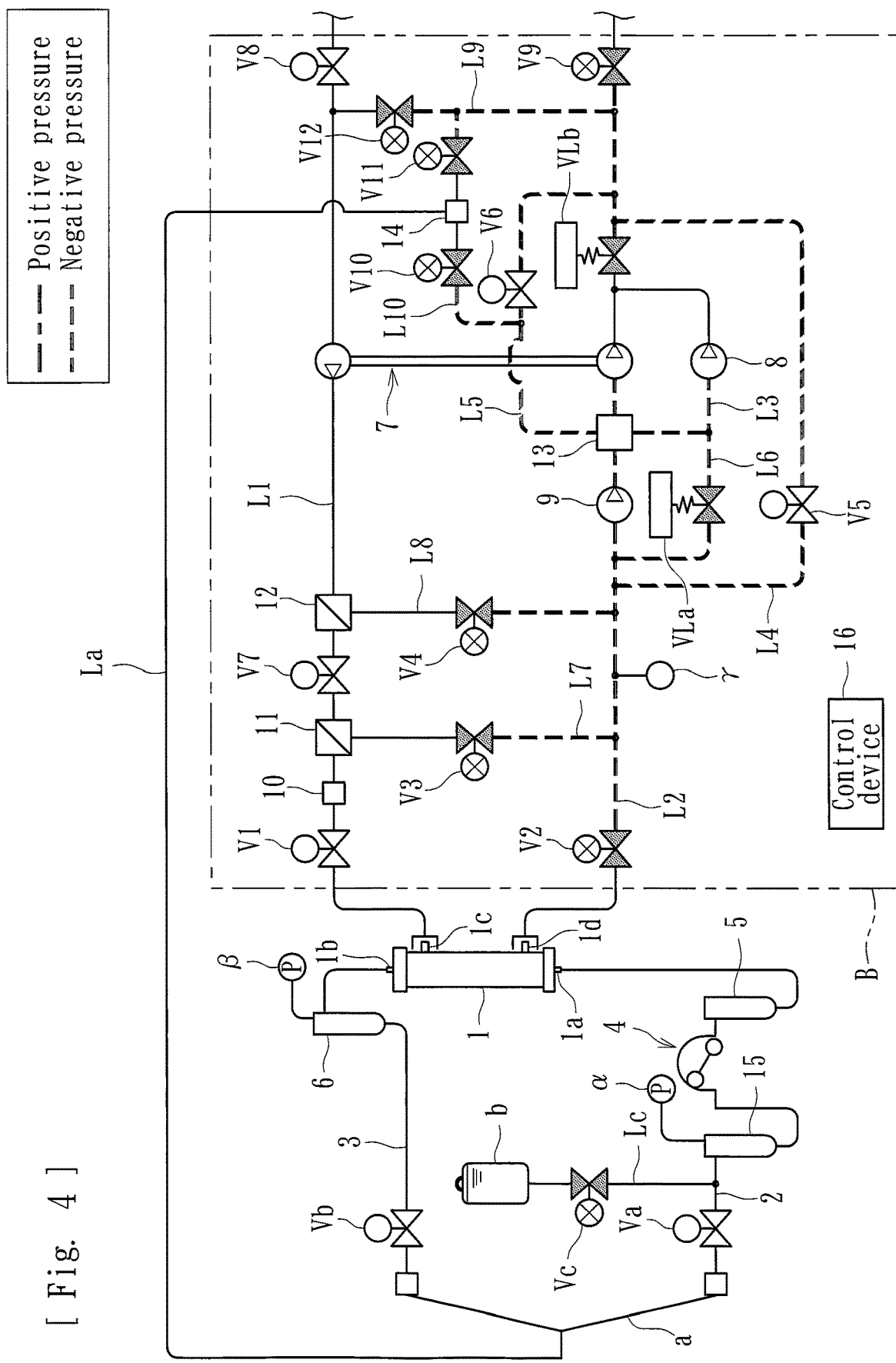
[Fig. 4]

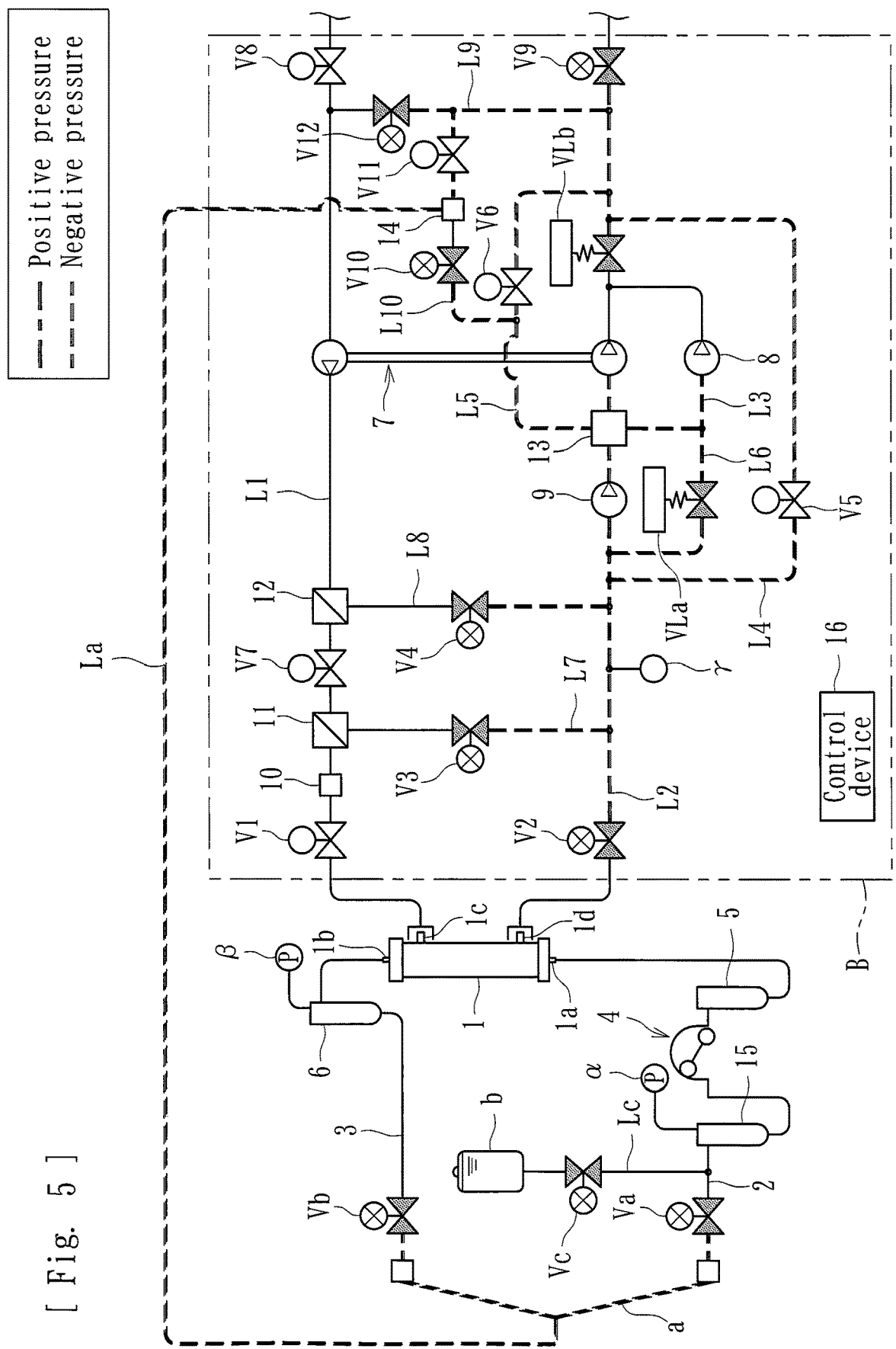
[Fig. 5]

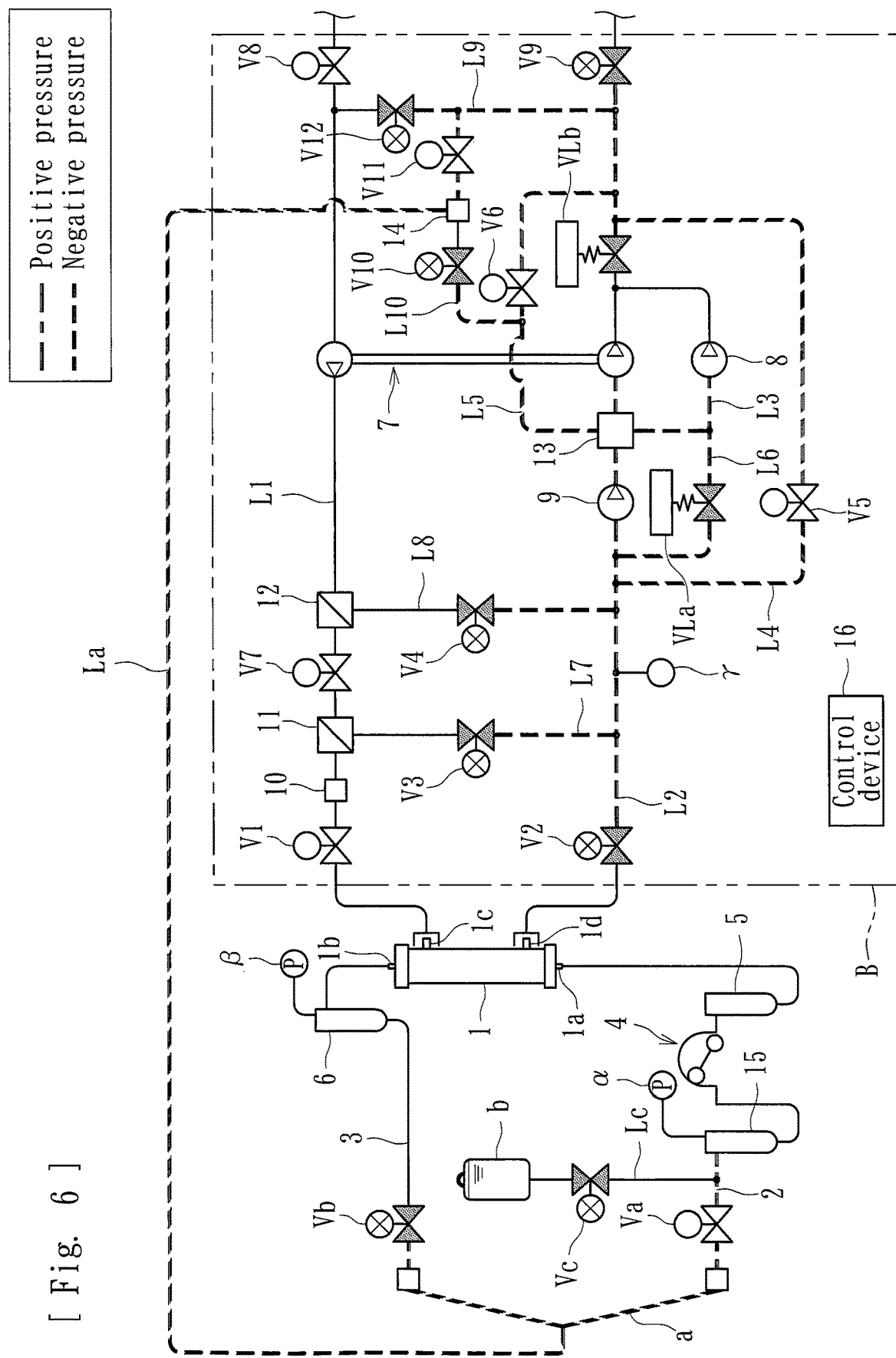
[Fig. 6]

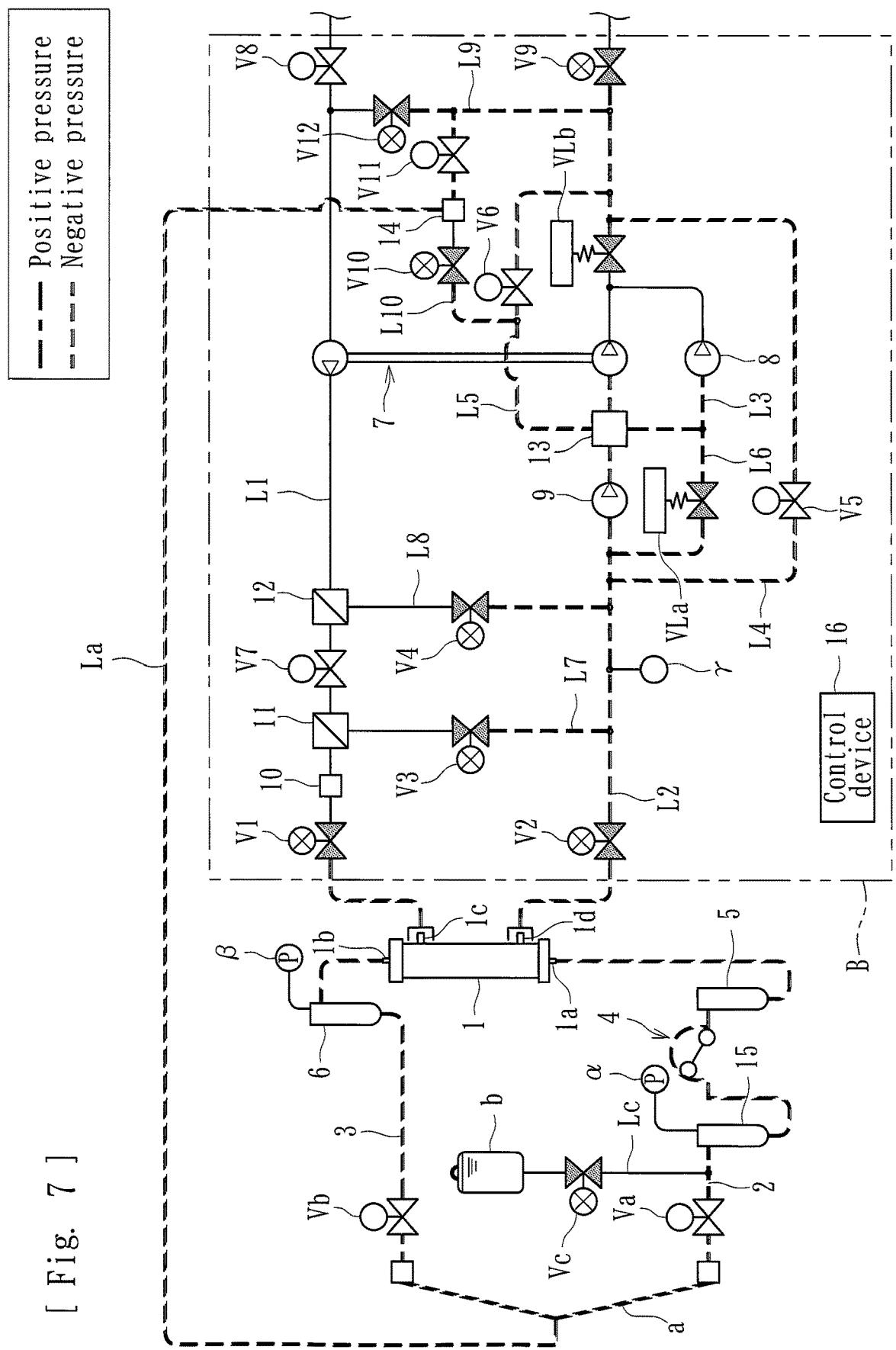
[Fig. 7]

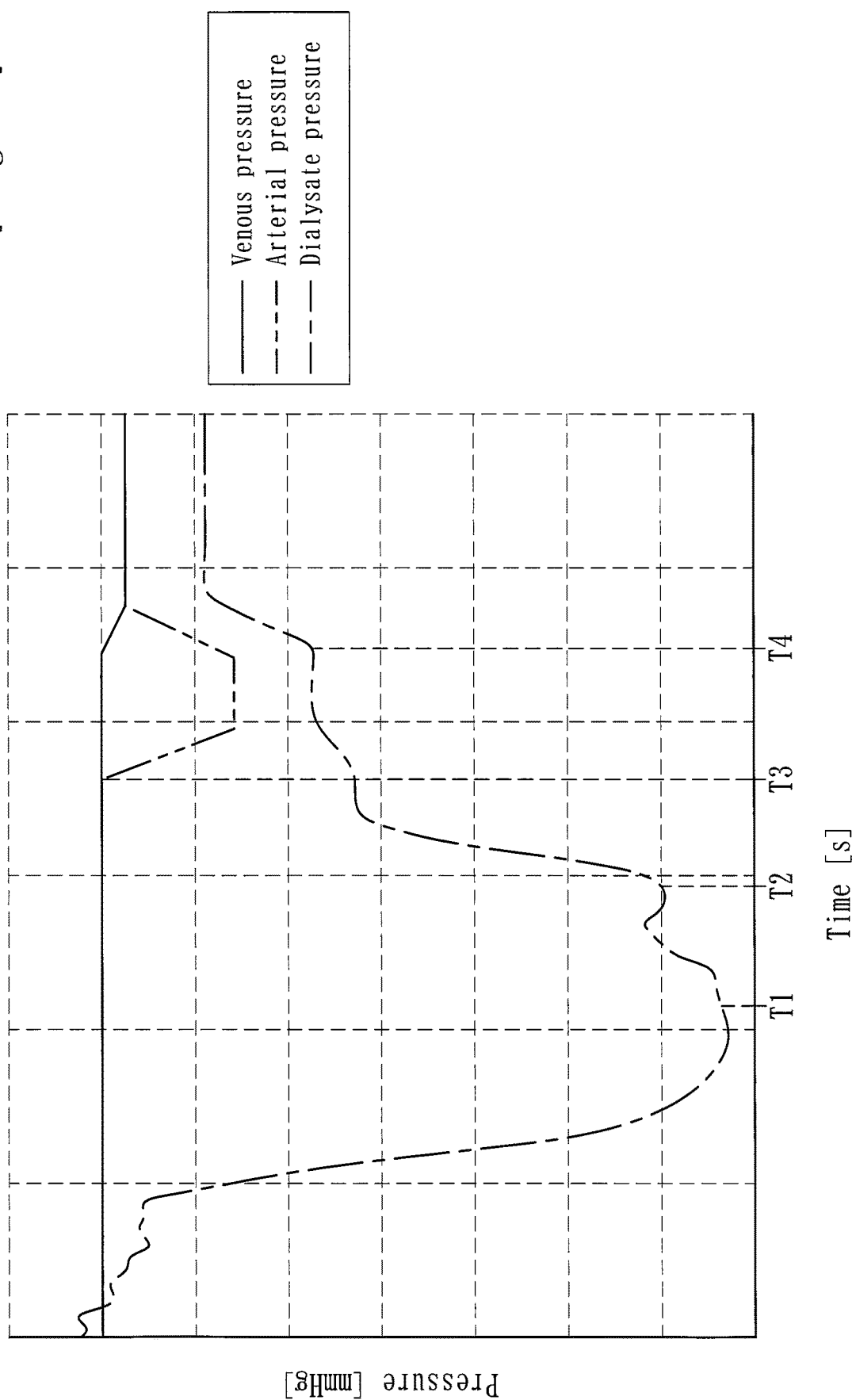
[Fig. 8]

[Fig. 9]
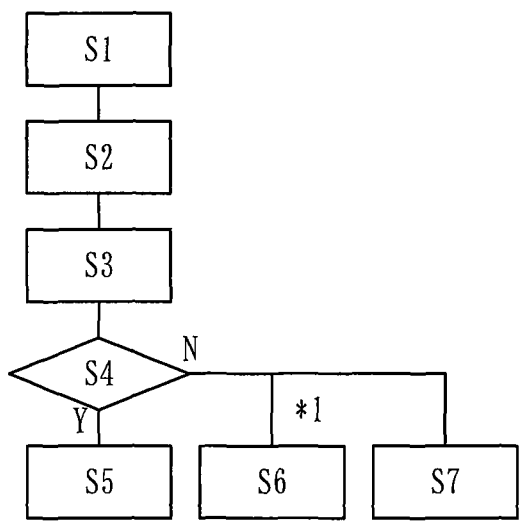
(S1) Pressure-applying step
(S2) Zero-value-acquiring step
(S3) Propagating step
(S4) Any pressure change?
(S5) Passed
(S6) Failed (unconnected)
(S7) Failed (Blockage)
(*1) Atmospheric pressure

[ Fig. 10 ]

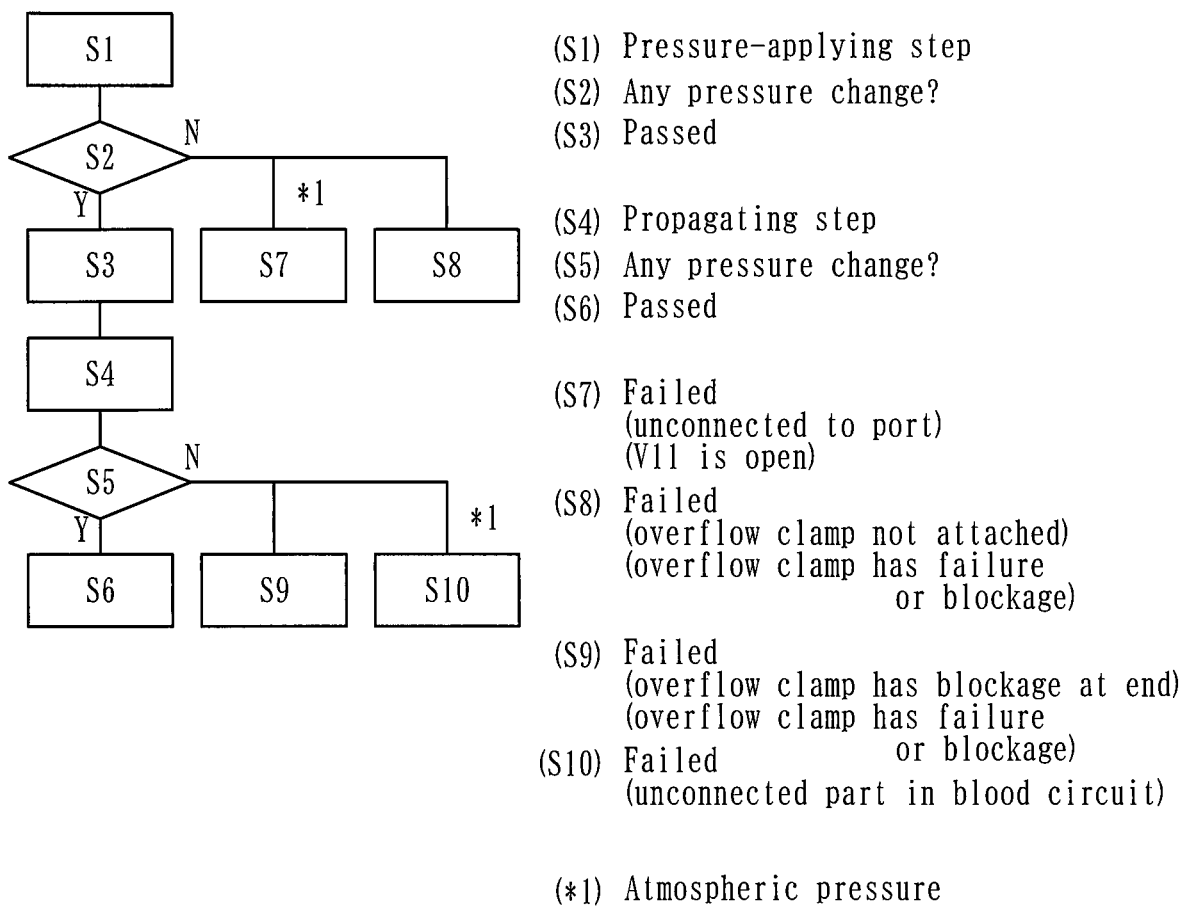

(S1) Pressure-applying step
(S2) Any pressure change?
(S3) Passed (S4) Propagating step
(S5) Any pressure change?
(S6) Passed (S7) Failed
    (unconnected to port)
    (V11 is open)
(S8) Failed
    (overflow clamp not attached)
    (overflow clamp has failure
                    or blockage)
(S9) Failed
    (overflow clamp has blockage at end)
    (overflow clamp has failure
                    or blockage)
(S10) Failed
    (unconnected part in blood circuit)

(*1) Atmospheric pressure

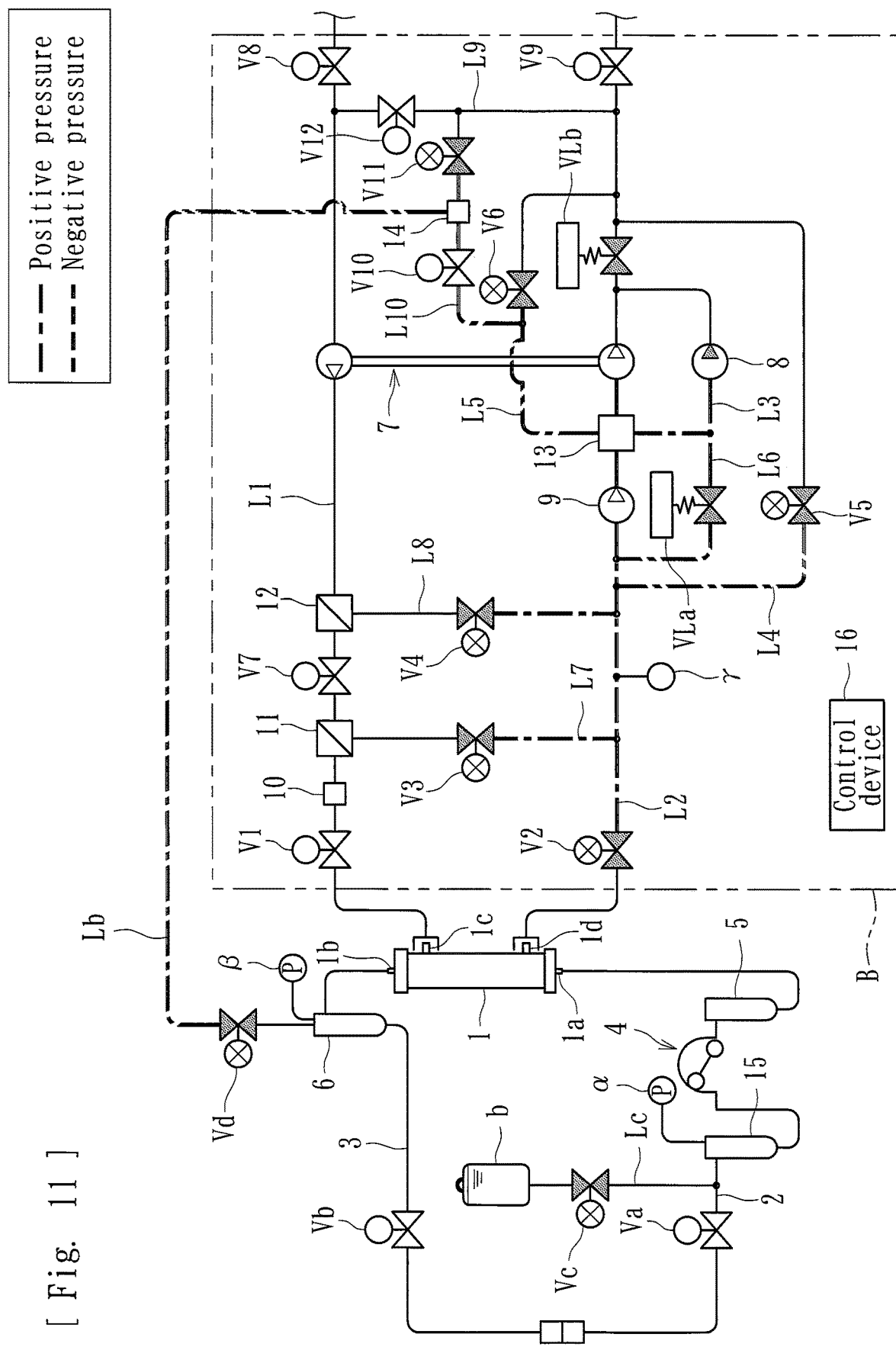
[Fig. 11]

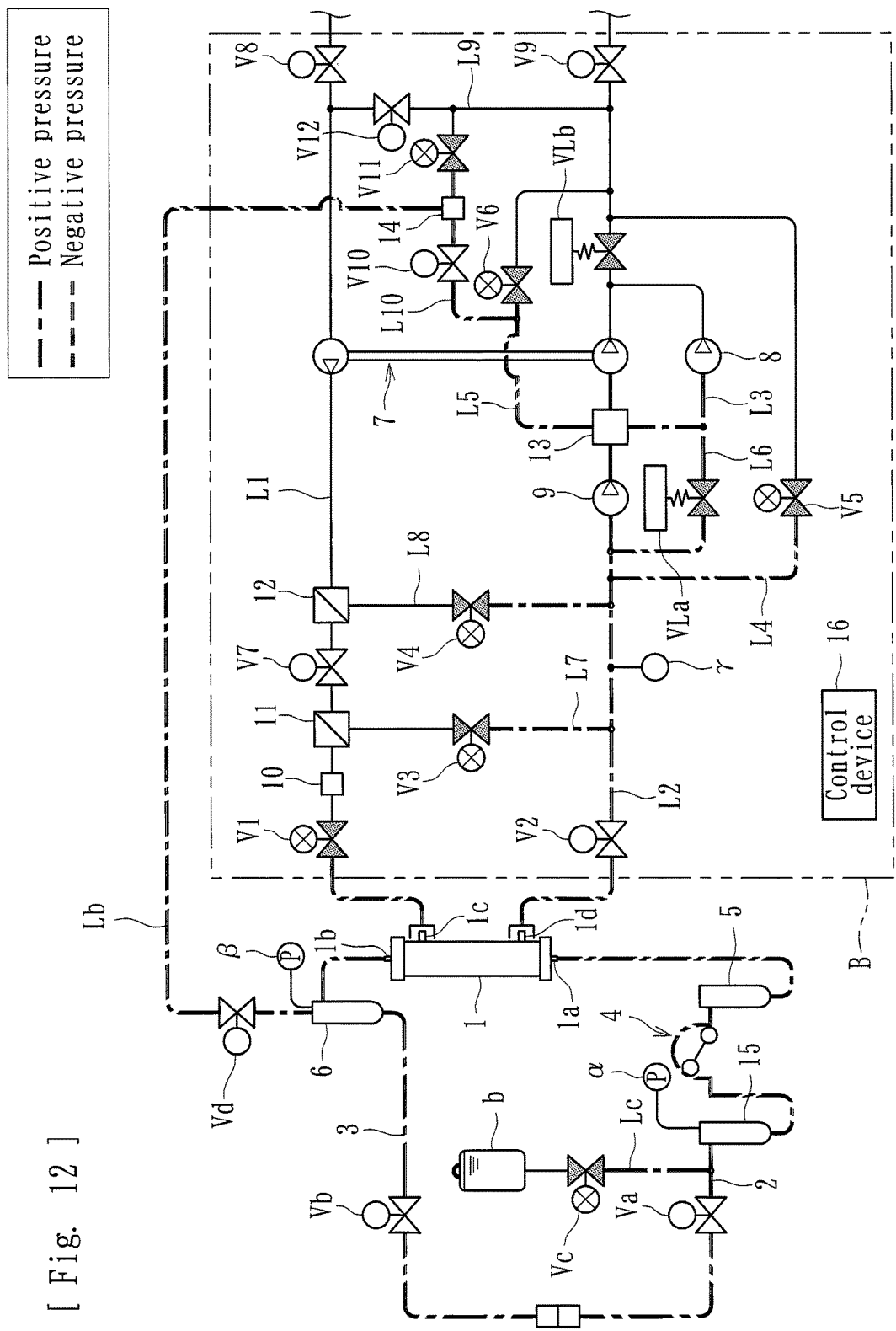
[Fig. 12]

[ Fig. 13 ]
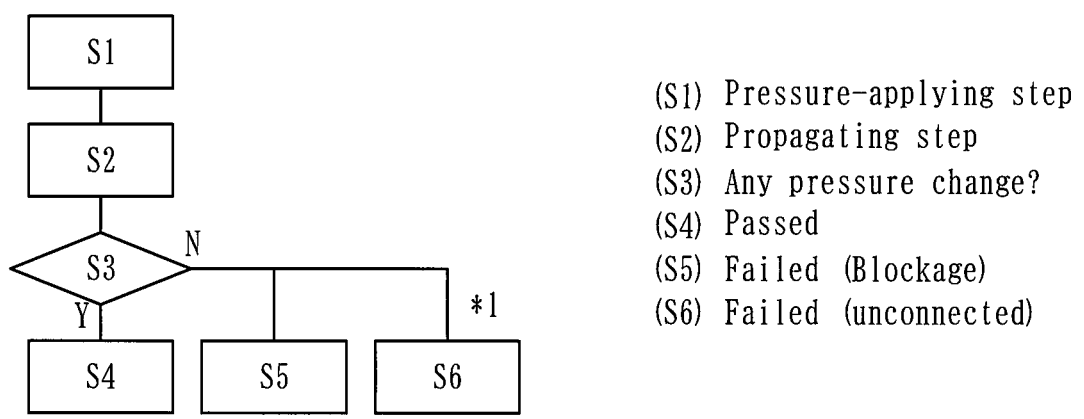
(S1) Pressure-applying step
(S2) Propagating step
(S3) Any pressure change?
(S4) Passed
(S5) Failed (Blockage)
(S6) Failed (unconnected)
(*1) Atmospheric pressure

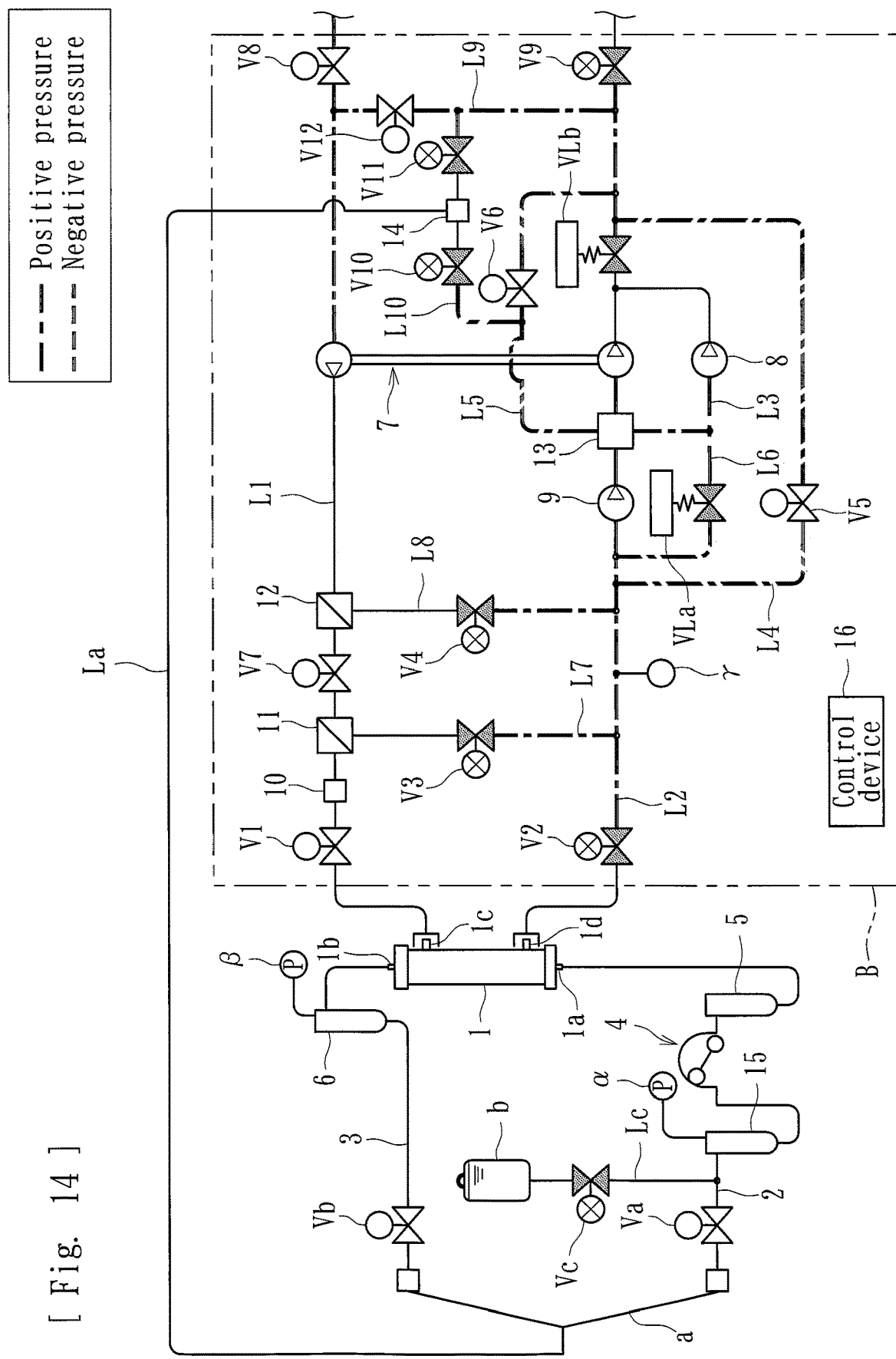
[Fig. 14]

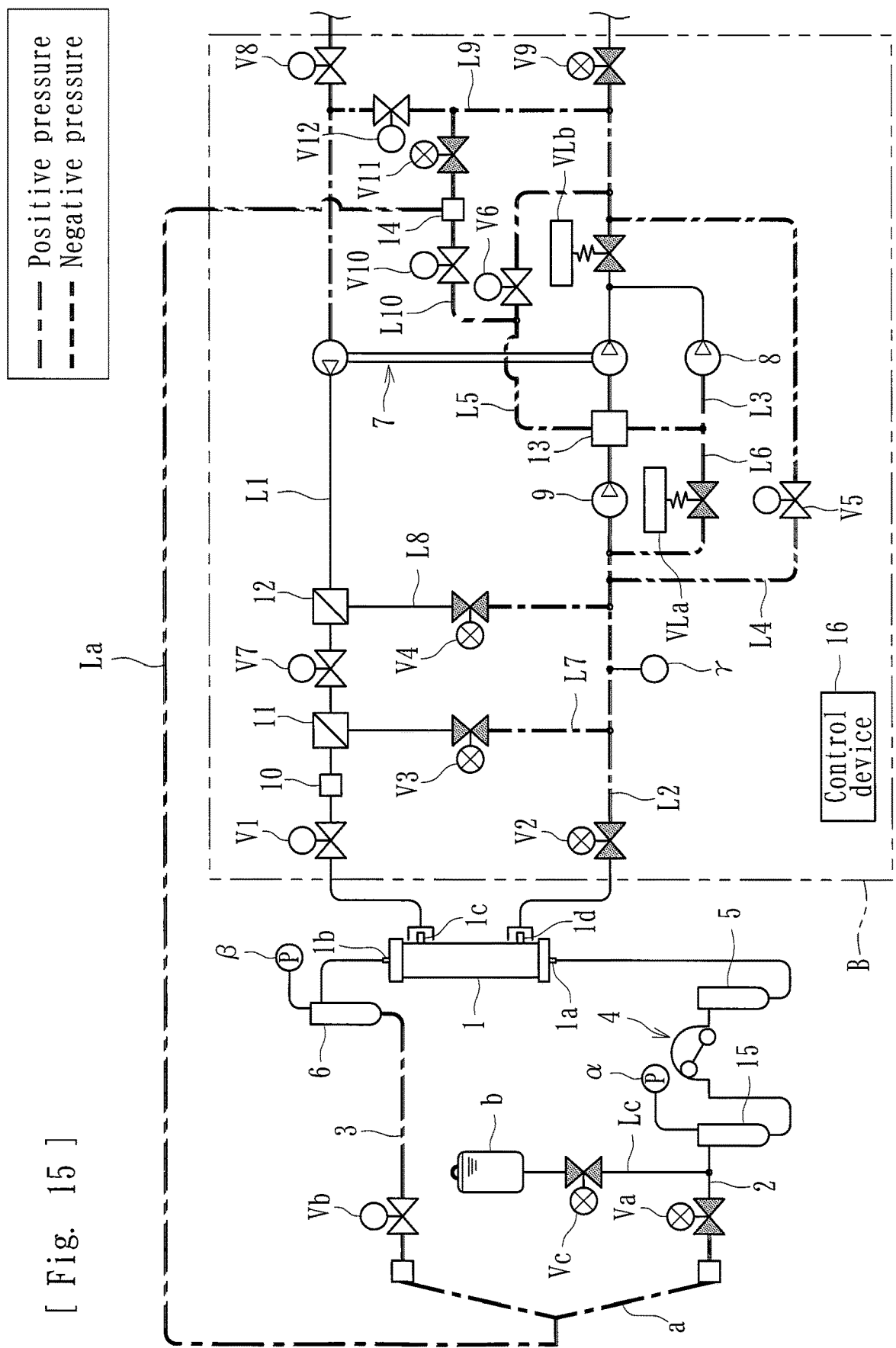
[Fig. 15]

[Fig. 16]

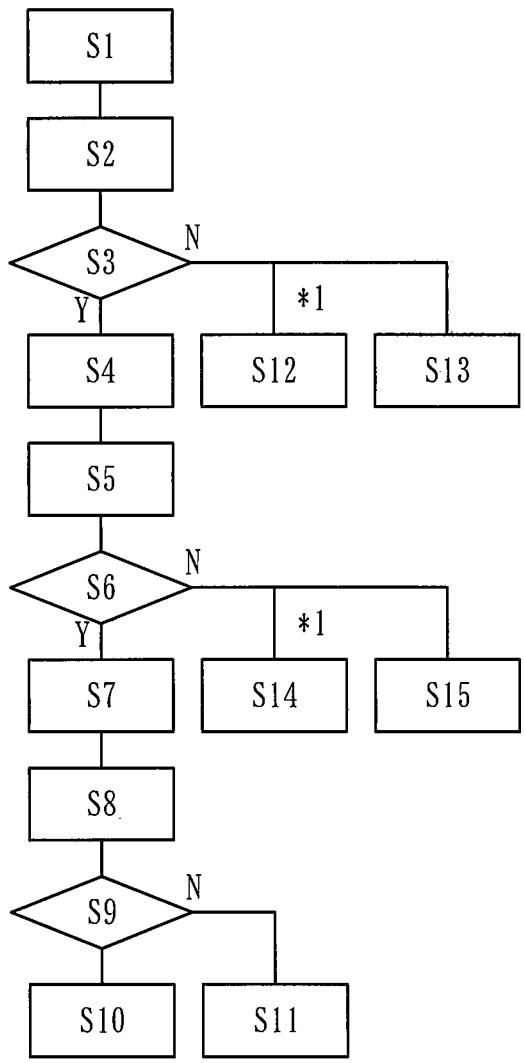

(S1) Pressure-applying step
(S2) Propagating step
(S3) Any pressure change?
(S4) Passed on venous side (S5) Propagating step
(S6) Any pressure change?
(S7) Passed on arterial side (S8) Open tube section
(S9) Any pressure change?
(S10) Passed
(S11) Failed
(blockage)

(S12) Failed
(venous side unconnected)
(S13) Failed
(blockage)
(venous clamp has failure)

(S14) Failed
(arterial side unconnected)
(S15) Failed
(arterial side has blockage)

(*1) Atmospheric pressure

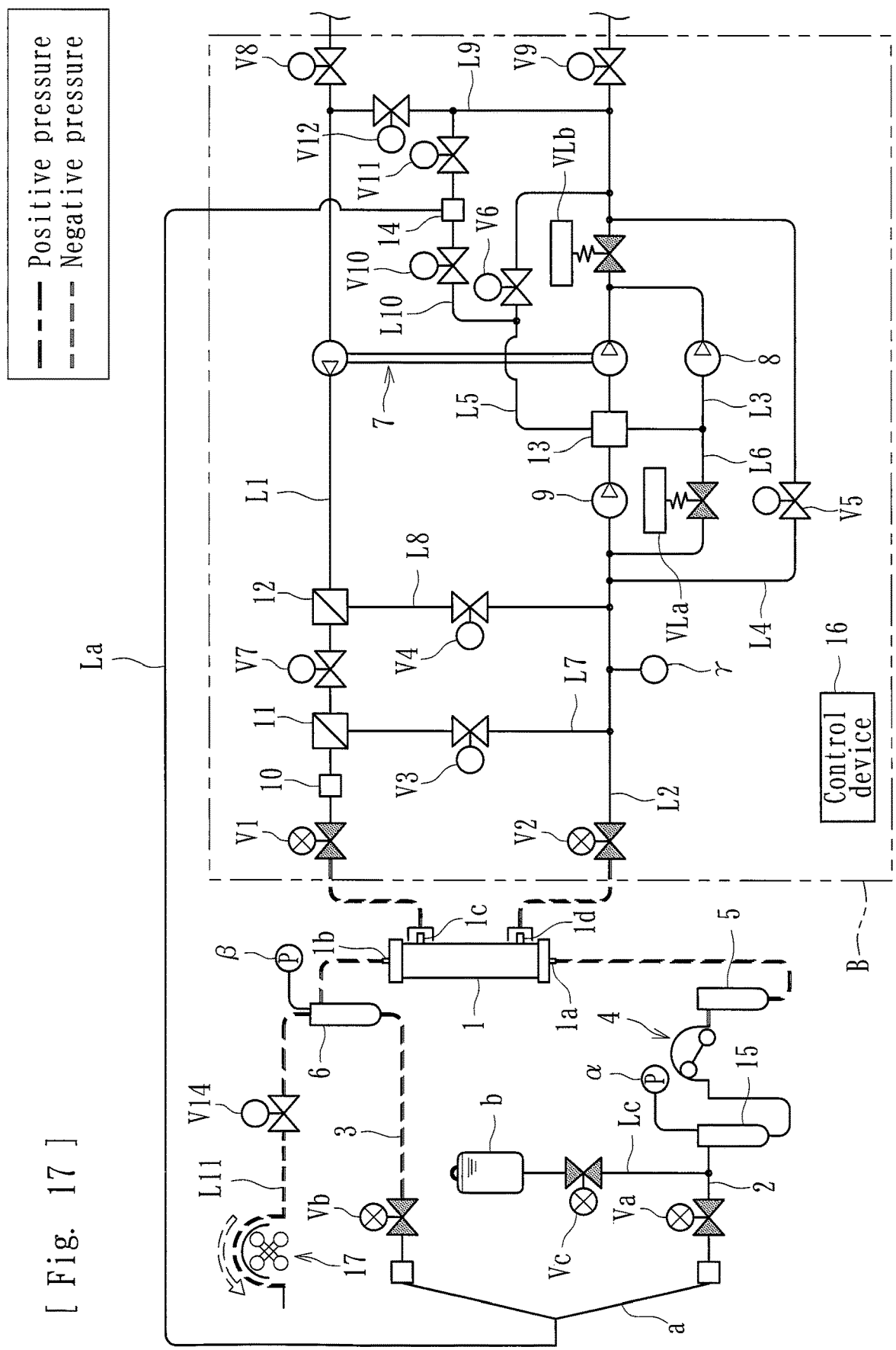
[Fig. 17]

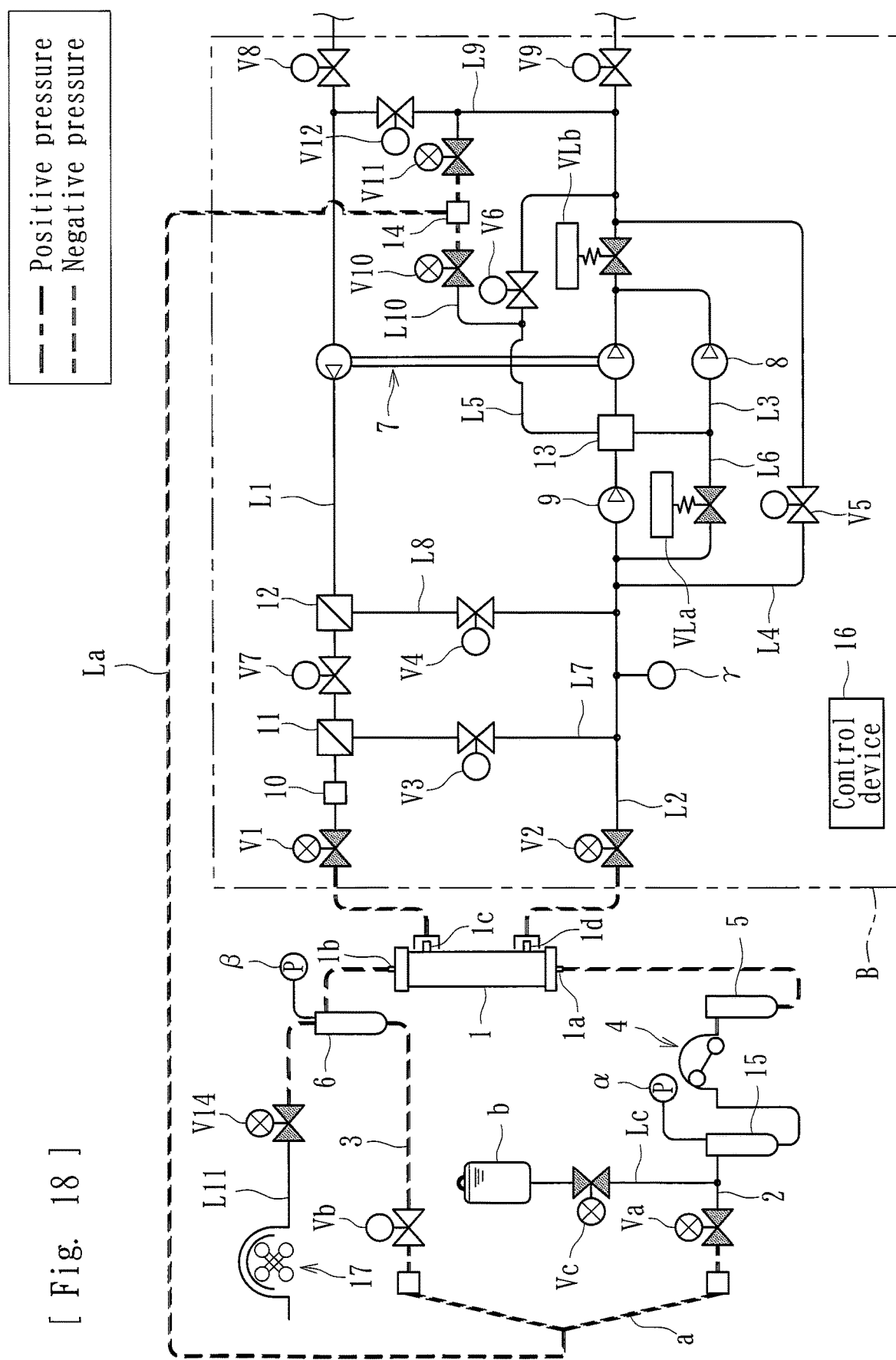
[Fig. 18]

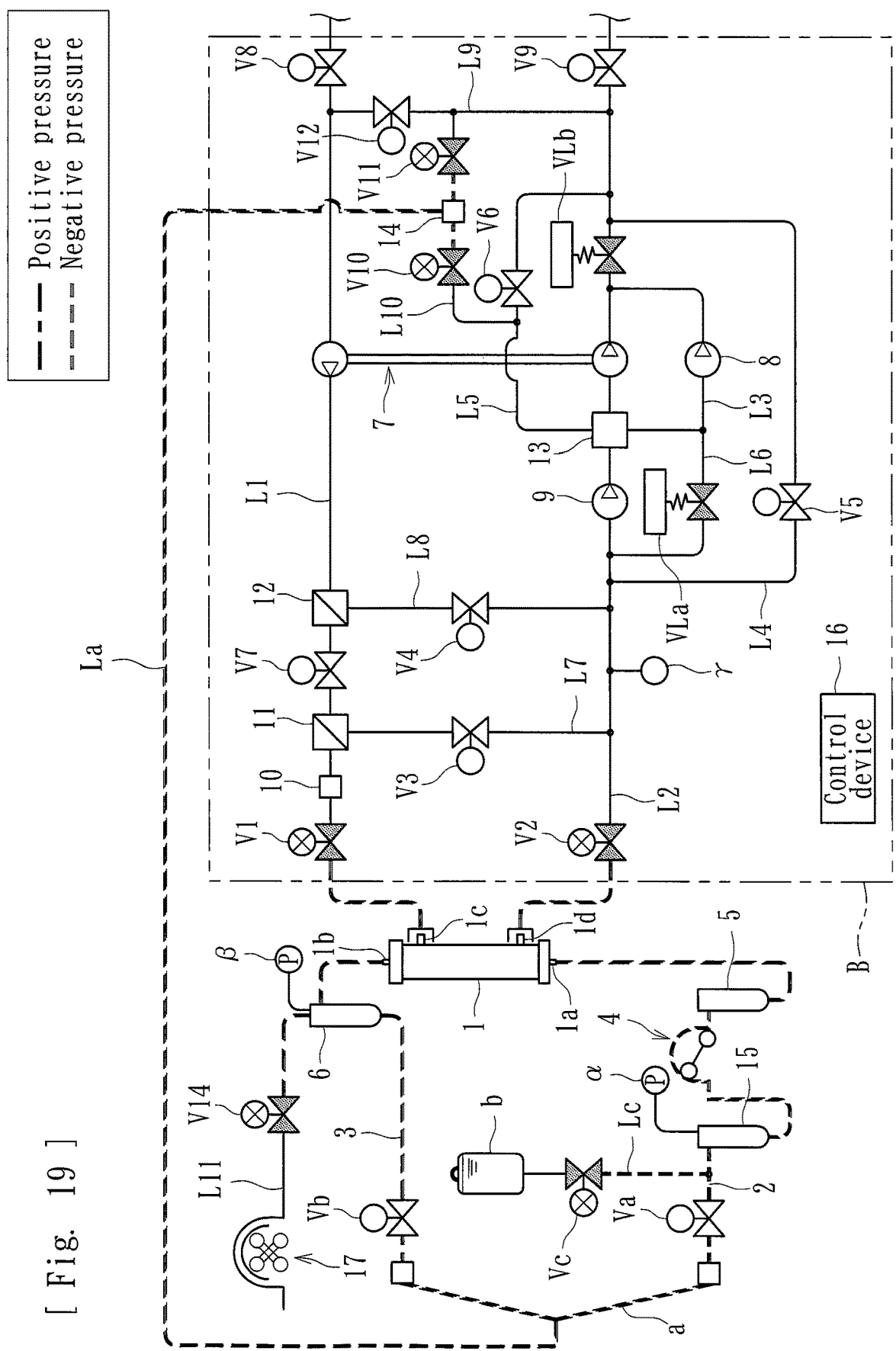
[Fig. 19]

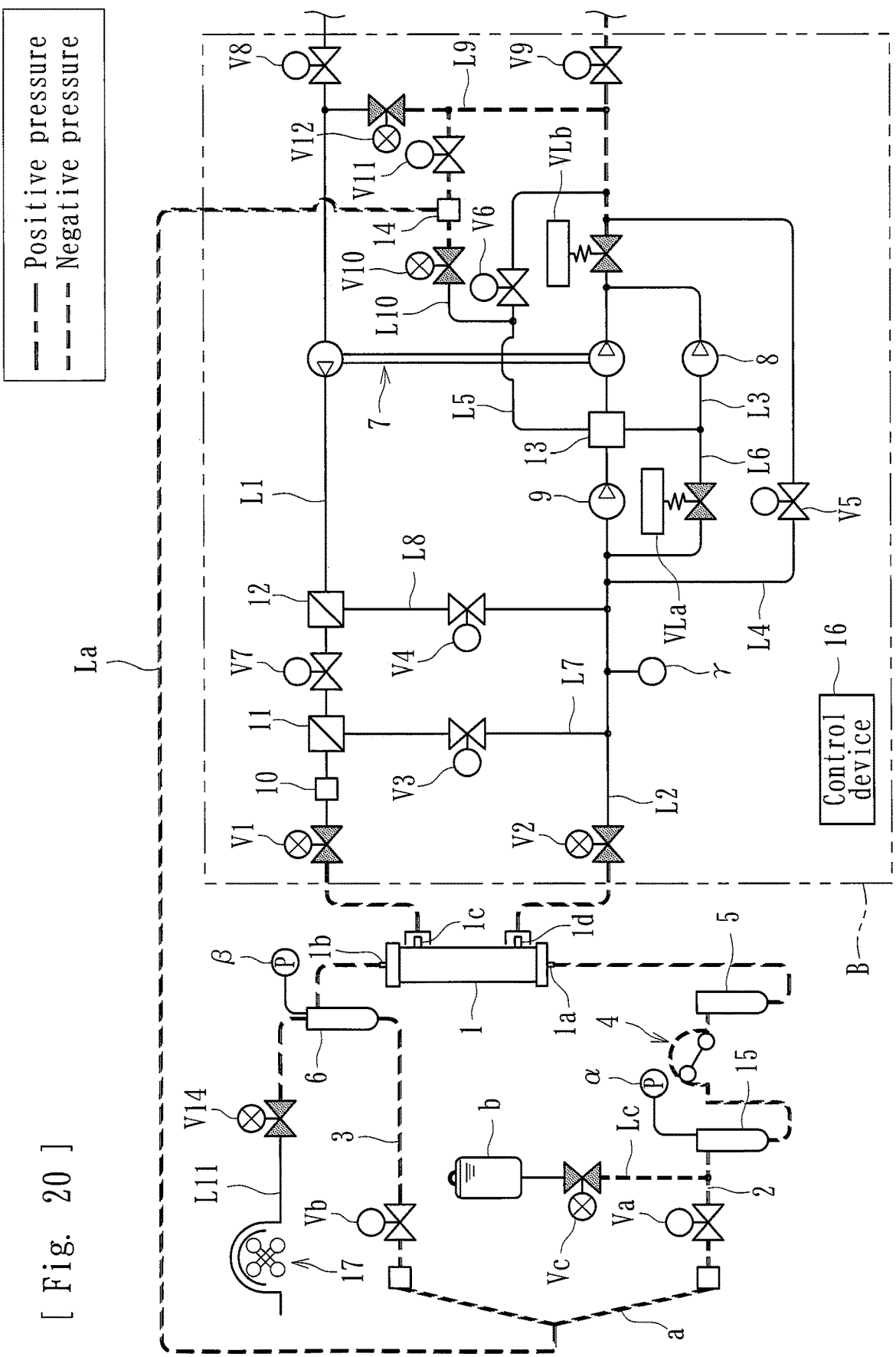
[Fig. 20]

BLOOD PURIFICATION APPARATUS

FIELD

The present invention relates to a blood purification apparatus for purifying blood of a patient while extracorporeally circulating the blood.

BACKGROUND

In recent years some techniques for dialysis apparatuses as blood purification apparatuses have been proposed, including a technique of performing priming with dialysate to be supplied into a dialyzer, blood returning, and substitution (emergency fluid infusion) in dialysis treatment, and a technique of using dialysate as a substitution solution for a treatment such as online HDF or online HF. For example, an apparatus proposed by PTL 1 includes a dialysate introduction line provided in a dialysis-apparatus body, and a dialysate supply line connected to a blood circuit, and dialysate in the dialysate introduction line is supplied into the blood circuit through the dialysate supply line, whereby priming, blood returning, and the like can be performed.

Another apparatus is also under consideration, which includes an overflow line connected to a dialysate drain line provided in a dialysis-apparatus body and to a blood circuit. The apparatus is capable of performing priming or the like by supplying a substitution solution, such as a physiological saline solution, into the blood circuit while draining the substitution solution into the dialysate drain line through the overflow line. As described above, recent proposals tend to provide a blood purification apparatus including a communicating line, such as a dialysate supply line or an overflow line, interposed between a tube section, including a dialysate introduction line and a dialysate drain line, provided in a dialysis-apparatus body and a blood circuit through which blood of a patient is extracorporeally circulated. The tube section of such a blood purification apparatus has a flow route thereinside. The blood circuit also has a flow route thereinside. The tube section or the blood circuit is provided with one or two or more clamping devices (such as electromagnetic valves) and one or two or more pumps.

PTL 1: Japanese Unexamined Patent Application Publication No. 2004-313522 the teaching of which are expressly incorporated by reference herein for all purposes.

SUMMARY

The above known blood purification apparatus has the following problem.

Typically, a connection-checking test for checking whether or not the blood circuit is normally connected to the dialysate drain line (the tube section) is conducted prior to, for example, priming. In a typical connection-checking test, prior to priming (that is, before the blood circuit is supplied and filled with the priming solution), a blood pump is activated so that the inside of the blood circuit and the overflow line (the communicating line) are pressurized, and a rise in the pressure in the blood circuit is detected by a venous-pressure sensor attached to, for example, a venous air-trap chamber. Furthermore, whether or not the detected pressure is retained for a predetermined period of time is checked. Thus whether or not the blood circuit is normally connected is checked.

In the above blood purification apparatus including the communicating line connected to the tube section in the dialysis-apparatus body and to the blood circuit, however, if a medical staff accidentally connects a distal end of an arterial blood circuit to a distal end of a venous blood circuit to form a closed circuit prior to the connection-checking test and if the blood circuit is pressurized in the connection-checking test, the venous pressure rises even if the communicating line is not connected to the tube section. Consequently, it may be determined that the connection is normal.

The present invention has been conceived in view of such circumstances and provides a blood purification apparatus in which whether or not the connection of a communicating line is appropriate can be determined more accurately.

According to the teachings herein, there is provided a blood purification apparatus that includes a blood circuit including an arterial blood circuit and a venous blood circuit through which blood of a patient is allowed to be extracorporeally circulated; a blood purification device provided between the arterial blood circuit and the venous blood circuit and that purifies the blood flowing in the blood circuit; a tube section including a dialysate introduction line and a dialysate drain line through which dialysate is introduced into and drained from the blood purification device, respectively; a pressure-detecting device that is capable of detecting a pressure in the tube section or a pressure in the blood circuit; a communicating line connected to the tube section and to the blood circuit and that allows a flow route of the tube section and a flow route of the blood circuit to communicate with each other; and a control device that is capable of controlling opening and closing of any of clamping devices included in the tube section or in the blood circuit and operation of any of pumps included in the tube section or in the blood circuit. The control device that performs the controlling is capable of executing a pressure-applying step in which a negative pressure or a positive pressure is applied to the flow route of one of the tube section and the blood circuit; a propagating step in which the negative pressure or the positive pressure applied in the pressure-applying step is propagated to the flow route of another of the tube section and the blood circuit through the communicating line; and a checking step in which whether or not the propagation of the negative pressure or the positive pressure in the propagating step is successful is checked with reference to the pressure detected by the pressure-detecting device, and in which whether or not the connection of the communicating line is appropriate is checked with reference to whether or not the propagation of the negative pressure or the positive pressure is successful.

According to the teachings herein, in the blood purification apparatus taught herein, not only whether or not the connection of the communicating line is appropriate but also whether or not the flow route of the blood circuit has any blockage is checked in the checking step.

According to the teachings herein, in the blood purification apparatus taught herein, the negative pressure or the positive pressure is applied to the flow route of the tube section in the pressure-applying step, and the negative pressure or the positive pressure is propagated to the flow route of the blood circuit through the communicating line in the propagating step.

According to the teachings herein, in the blood purification apparatus taught herein, the negative pressure is applied to the flow route of the tube section in the pressure-applying step.

According to the teachings herein, in the blood purification apparatus taught herein, the negative pressure or the positive pressure is applied to the flow route of the blood circuit in the pressure-applying step, and the negative pressure or the positive pressure is propagated to the flow route of the tube section through the communicating line in the propagating step.

According to the teachings herein, in the blood purification apparatus taught herein, the communicating line is connectable to a connection port provided to the dialysate drain line or to a branch line branching off from the dialysate drain line in the tube section.

According to the teachings herein, the control device that performs the controlling is capable of executing the pressure-applying step in which a negative pressure or a positive pressure is applied to the flow route of one of the tube section and the blood circuit; the propagating step in which the negative pressure or the positive pressure applied in the pressure-applying step is propagated to the flow route of the other of the tube section and the blood circuit through the communicating line; and the checking step in which whether or not the propagation of the negative pressure or the positive pressure in the propagating step is successful is checked with reference to the pressure detected by the pressure-detecting device, and in which whether or not the connection of the communicating line is appropriate is checked with reference to whether or not the propagation of the negative pressure or the positive pressure is successful. Hence, whether or not the connection of the communicating line is appropriate can be determined more accurately.

According to the teachings herein, not only whether or not the connection of the communicating line is appropriate but also whether or not the flow route of the blood circuit has any blockage is checked in the checking step. Hence, whether or not the connection of the communicating line is appropriate and whether or not there is any blockage in the blood circuit can be determined accurately.

According to the teachings herein, the negative pressure or the positive pressure is applied to the flow route of the tube section in the pressure-applying step, and the negative pressure or the positive pressure is propagated to the flow route of the blood circuit through the communicating line in the propagating step. Hence, regardless of the state of the blood circuit (for example, even in a state where the blood circuit is being inserted in the patient), whether or not the connection of the communicating line is appropriate can be determined accurately.

According to the teachings herein, the negative pressure is applied to the flow route of the tube section in the pressure-applying step. Accordingly, the negative pressure generated in the tube section propagates to the blood circuit. Hence, the occurrence of a situation where a positive pressure is propagated and the dialysate in the tube section accidentally flows into the blood circuit can be prevented.

According to the teachings herein, the negative pressure or the positive pressure is applied to the flow route of the blood circuit in the pressure-applying step, and the negative pressure or the positive pressure is propagated to the flow route of the tuba section through the communicating line in the propagating step. Hence, regardless of the state of the tube section, whether or not the connection of the communicating line is appropriate can be determined accurately.

According to the teachings herein, the communicating line is connectable to the connection port provided to the dialysate drain line or to a branch line branching off from the dialysate drain line in the tube section. Hence, for example, during priming, the priming solution in the blood circuit can be drained into the dialysate drain line or into the branch line branching off therefrom. Furthermore, in the connection-checking test, whether or not the connection of the communicating line is appropriate can be determined accurately.

BRIEF DESCRIPTION OF THE DRAWINGS

FIG. 1 is a schematic diagram of a blood purification apparatus according to a first embodiment of the present invention.

FIG. 2 is a flow chart of a control process executed by the blood purification apparatus.

FIG. 3 is a schematic diagram of the blood purification apparatus in a state during a connection-checking test.

FIG. 4 is a schematic diagram of the blood purification apparatus in another state during the connection-checking test.

FIG. 5 is a schematic diagram of the blood purification apparatus in yet another state during the connection-checking test.

FIG. 6 is a schematic diagram of the blood purification apparatus in yet another state during the connection-checking test.

FIG. 7 is a schematic diagram of the blood purification apparatus in yet another state during the connection-checking test.

FIG. 8 is a graph illustrating changes in pressures measured in the blood purification apparatus during the connection-checking test.

FIG. 9 is a flow chart of a control process executed by a blood purification apparatus according to a second embodiment of the present invention.

FIG. 10 is a flow chart of a control process executed by a blood purification apparatus according to a third embodiment of the present invention.

FIG. 11 is a schematic diagram of the blood purification apparatus in a state during a connection-checking test.

FIG. 12 is a schematic diagram of the blood purification apparatus in another state during the connection-checking test.

FIG. 13 is a flow chart of a control process executed by a blood purification apparatus according to a fourth embodiment of the present invention.

FIG. 14 is a schematic diagram of the blood purification apparatus in a state during a connection-checking test.

FIG. 15 is a schematic diagram of the blood purification apparatus in another state during the connection-checking test.

FIG. 16 is a flow chart of a control process executed by a blood purification apparatus according to a fifth embodiment of the present invention.

FIG. 17 is a schematic diagram of the blood purification apparatus in a state during a connection-checking test.

FIG. 18 is a schematic diagram of the blood purification apparatus in another state during the connection-checking test.

FIG. 19 is a schematic diagram of the blood purification apparatus in yet another state during the connection-checking test.

FIG. 20 is a schematic diagram of the blood purification apparatus in yet another state during the connection-checking test.

DETAILED DESCRIPTION

Embodiments of the present invention will now be described specifically with reference to the drawings.

A blood purification apparatus according to a first embodiment is used in blood purification treatment (hemodialysis treatment) in which blood of a patient can be purified while being extracorporeally circulated. As illustrated in FIG. 1, the apparatus includes a blood circuit including an arterial blood circuit 2 and a venous blood circuit 3 through which the blood of the patient is allowed to be extracorporeally circulated, a dialyzer 1 (a blood purification device) provided between the arterial, blood circuit 2 and the venous blood circuit 3 and that purifies the blood flowing in the blood circuit, a tube section including a dialysate introduction line L1 and a dialysate drain line L2 provided in a dialysis-apparatus body B, and a control device 16.

The dialyzer 1 is provided for purifying blood. The dialyzer 1 is connected to the arterial blood circuit 2 and the venous blood circuit 3 of the blood circuit at respective ports 1a and 1b thereof and to the dialysate introduction line L1 and the dialysate drain line L2 at respective ports 1c and 1d thereof. The arterial blood circuit 2 is provided with a blood pump 4 that is a peristaltic pump. When the blood pump 4 is activated, liquid such as dialysate can be delivered through the blood circuit.

The arterial blood circuit 2 and the venous blood circuit 3 are connectable at the distal ends thereof to an arterial puncture needle and a venous puncture needle, respectively. When the blood pump 4 is activated with the arterial puncture needle and the venous puncture needle being inserted in the patient, the blood of the patient collected through the arterial puncture needle is extracorporeally circulated through the blood circuit, is purified and ultrafiltered in the dialyzer 1, and is returned to the patient through the venous puncture needle.

The arterial blood circuit 2 is provided with a storage bag b that stores a physiological saline solution (a substitution solution used in priming, blood returning, or the like) at a position between a clamping device Va and the blood pump 4 and with a supply line Lc interposed therebetween. When a clamping device Vc provided at a halfway position of the supply line Lc is opened, the physiological saline solution in the storage bag (b) is supplied to the arterial blood circuit 2, whereby priming of the blood circuit, blood returning, or the like can be performed. The substitution solution to be supplied to the blood circuit is not limited to a physiological saline solution and may be any other substitution solution.

The arterial blood circuit 2 is provided with a pressure-detecting device (α) connected to a position thereof on the upstream side with respect to the blood pump 4 (between the blood pump 4 and the clamping device Va) with a chamber 15 interposed therebetween. The pressure-detecting device (α) is capable of detecting the pressure (the liquid pressure) at that position and thus measuring the arterial pressure (the blood-extraction pressure) during the treatment. The arterial blood circuit 2 is also provided with an air-trap chamber 5 and with the clamping device Va on the distal side thereof (on the upstream side with respect to the position of the arterial blood circuit 2 where the supply line Lc is connected). The venous blood circuit 3 is provided with an air-trap chamber 6 and with a clamping device Vb on the distal side thereof (on the downstream side with respect to a position of the venous blood circuit 3 where the air-trap chamber 6 is connected). The air-trap chamber 6 is provided with a pressure-detecting device (β) that is capable of detecting the venous pressure in the blood circuit during the treatment. That is, the pressure (the arterial pressure) in the arterial blood circuit 2 is detectable by the pressure-detecting device (α), and the pressure (the venous pressure) in the venous blood circuit 3 is detectable by the pressure-detecting device (β).

The dialysate introduction line L1 and the dialysate drain line L2 are provided with a duplex pump 7 serving as a liquid-delivering pump that supplies a dialysate prepared to have a predetermined concentration into the dialyzer 1 and drains the dialysate from the dialyzer 1. That is, the duplex pump 7 is provided over the dialysate introduction line L1 and the dialysate drain line L2. When the duplex pump 7 is actuated, the duplex pump 7 introduces the dialysate into the dialyzer 1 through the dialysate introduction line L1 while draining the dialysate from the dialyzer 1 through the dialysate drain line L2.

The dialysate introduction line L1 is provided with filters 11 and 12, where the dialysate to be introduced into the dialyzer 1 can be filtered. Meanwhile, the flow route of the dialysate introduction line L1 is closable and openable at an arbitrary timing by using electromagnetic valves V1, V7, and V8. The dialysate introduction line L1 is connected to the dialysate drain line L2 with bypass lines L7, L8, and L9. The bypass lines L7, L8, and L9 are provided with electromagnetic valves V3, V4, and V12, respectively. The dialysate introduction line L1 is also provided with a collecting port 10 (a sampling port) from which the dialysate flowing in the dialysate introduction line L1 is collectable.

The flow route of the dialysate drain line L2 is closable and openable at an arbitrary timing by using electromagnetic valves V2 and V9. The dialysate drain line L2 is connected to detour lines L3 and L4 that detour the duplex pump 7. The detour line L3 is provided with an ultrafiltration pump 8. The detour line L4 is provided with an electromagnetic valve V5. Hence, when the ultrafiltration pump 8 is activated in the process extracorporeally circulating the blood of the patient through the blood circuit, ultrafiltration can be performed in which water is removed from the blood flowing in the dialyzer 1.

The dialysate drain line L2 is provided with a pressurizing pump 9 on the upstream side (the left side in the drawing) thereof with respect to the duplex pump 7. The pressurizing pump 9 adjusts the liquid pressure in the dialysate drain line L2 at the duplex pump 7. The dialysate drain line L2 is also provided with a detour line L5 extending from a position thereof between the pressurizing pump 9 and the duplex pump 7 and with a degassing chamber 13 interposed therebetween. The degassing chamber 13 catches bubbles in the dialysate flowing in the dialysate drain line L2 that is on the upstream side with respect to the duplex pump 7 and allows the bubbles to be discharged to the outside while detouring the duplex pump 7.

The detour line L5 is provided with an electromagnet valve V6 and a branch line L10. The branch line L10 extends between a position of the detour line L5 that is on the upstream side with respect to the electromagnetic valve V6 (between the degassing chamber 13 and the electromagnetic valve V6) and the bypass line L9 and allows the flow routes of the detour line L5 and the bypass line L9 to communicate with each other. The branch line L10 is provided with an electromagnetic valve V10 and air electromagnetic valve V11. A connection port 14 to which an end of a communicating line La is connectable is provided between the electromagnetic valves V10 and V11. One end of the communicating line La is connected to the connection port 14, and the other end of the communicating line La is connected to the blood circuit with a wye tube a interposed therebetween. Thus, the liquid (the substitution solution such as a physiological saline solution) in the blood circuit is allowed to flow to the dialysate drain line L2.

The dialysate drain line L2 is also provided with a pressure-detecting device (γ) connected to a position thereof on the downstream side with respect to the electromagnetic valve V2 (between the connection to the bypass line L7 and the connection to the bypass line L8). The pressure-detecting device (γ) is a sensor capable of detecting the pressure (the dialysate pressure) in the tube section. The dialysate drain line L2 is also provided with a detour line L6 extending from a position thereof between the connection to the detour line L4 and the pressurizing pump 9 up to the detour line L3. The detour line L6 is provided with a relief valve VLa. The dialysate drain line L2 is also provided with a back-pressure valve VLb at a position thereof on the downstream side with respect to the duplex pump 7 and between the connection to the detour line L3 and the connection to the detour line L4.

The dialysis-apparatus body B includes the tube section and the control device 16. The tube section includes the dialysate introduction line L1 through which the dialysate is introduced into the dialyzer 1, and the dialysate drain line L2 through which the dialysate is drained from the dialyzer 1. The tube section according to the present invention includes not only the dialysate introduction line L1 and the dialysate drain line L2 but also the detour lines (L3, L4, L5, and L6), the bypass lines (L7, L8, and L9), the branch line L10, and the like each branching off from the dialysate introduction line L1 or from the dialysate drain line L2. The tube section allows the dialysate or the like to flow therethrough.

The control device 16 is a microcomputer or the like provided in the dialysis-apparatus body B and is capable of controlling the opening and closing of any of the clamping devices (such as the electromagnetic valves) and the operation of any of the pumps in the tube section and in the blood circuit, thereby enabling the blood purification treatment and operations to be performed before and after the treatment. The communicating line La is a flow route connected to the tube section provided in the dialysis-apparatus body B and to the bloc) d circuit and allows the flow route in the tube section and the flow route in the blood circuit to communicate with each other. The communicating line La according to the present embodiment allows the arterial blood circuit 2 and the venous blood circuit 3 to communicate, through the wye tube (a), with the branch line L10 branching off from the dialysate drain line L2.

For example, in the blood purification apparatus according to the present embodiment, when priming to be performed prior to the blood purification treatment is performed, the wye tube a is connected to the respective distal ends of the arterial blood circuit 2 end the venous blood circuit 3. Furthermore, one end of the communicating line La is connected to the distal end of the wye tube, while the other end of the communicating line La is connected to the connection port 14. In this state, the control device 16 controls any of the clamping devices (the electromagnetic valves) and the pumps to activate, whereby the physiological saline solution in the storage bag b is supplied and filed into the blood circuit while being drained from the connection port 14 into the dialysate drain line L2.

The control device 16 according to the present embodiment is capable of executing a connection-checking test on the communicating line La prior to priming. The connection-checking test includes, as illustrated in FIG. 2, a pressure-applying step S1 in which a negative pressure or a positive pressure (in the present embodiment, a negative pressure) is applied to the flow route of one of the tube section and the blood circuit (in the present embodiment, the flow route of the tube section), a propagating step S3 in which the negative pressure or the positive pressure applied in the pressure-applying step S1 is propagated to the flow route of the other of the tube section and the blood circuit (in the present embodiment, the flow route of the blood circuit) through the communicating line La, and a checking step (S5) in which whether or not the propagation of the negative pressure or the positive pressure in the propagating step S3 is successful is checked with reference to the pressures detected by the pressure-detecting devices (in the present embodiment, the pressure-detecting devices (α), (β), and (γ)), and in which whether or not the connection of the communicating line La is appropriate is checked with reference to whether or not the propagation of the negative pressure or the positive pressure is successful.

Now, a specific control process executed in the connection-checking test by the control device 16 according to the first embodiment will be described with reference to the flow chart illustrated in FIG. 2.

First, as illustrated in FIG. 1, the wye tube a is connected to the distal ends of the arterial blood circuit 2 and the venous blood circuit 3, and the communicating line La is connected to the distal end of the wye tube a and to the connection port 14 (a state for performing priming). In the tube section, as illustrated in FIG. 3, the electromagnetic valves (V2, V3, V4, V5, V10, V11, and V8 or V12) are closed while the electromagnetic valves (V6 and V9) are opened. In this state, the pressurizing pump 9 is activated. Thus, a negative-pressure portion is formed in a predetermined part of the tube section (the pressure-applying step S1). Note that the clamping device Vc is kept closed during the connection-checking test. The other electromagnetic valves (the electromagnetic valves V1, V7, and others) in the tube section and the electromagnetic valves and the clamping devices in the blood circuit may each be either opened or closed. During the connection-checking test, the duplex pump 7 is kept stopped, and the relief valve VLa and the back-pressure valve VLb are closed.

Subsequently, as illustrated in FIG. 4, the electromagnetic valve V5 is opened, and the electromagnetic valve V9 is closed. Then, the pressures (the arterial pressure, the venous pressure, and the dialysate pressure) detected by the pressure-detecting devices ((α), (β), and (γ)) in this state are stored (a zero-value-acquiring step S2). Furthermore, as illustrated in FIG. 5, while the clamping devices (Va and Vb) in the blood circuit are closed, the electromagnetic valve V11 in the tube section is opened. Thus, the negative pressure in the negative-pressure portion formed in the pressure-applying step S1 is propagated to the blood circuit through the communicating line La (the propagating step S3).

After the step S3, the clamping device Va in the blood circuit is opened (S4) as illustrated in FIG. 6. Then, whether or not there is any change by a predetermined value or greater (any drop by a predetermined value or greater) in the pressure (the arterial pressure) detected by the pressure-detecting device α from the pressure stored in the zero-value-acquiring step S2 is checked (S5). If there is a change by the predetermined value or greater, it is regarded that the negative pressure in the negative-pressure portion has been propagated normally to the blood circuit (the arterial blood circuit 2) through the communicating line La. Hence, the process proceeds to a step S6, where it is determined that the test is passed (the connection of the communicating line La and the connection in the portion from the distal end of the arterial blood circuit 2 to the blood pump 4 are appropriate with no blockage) (S6).

After the step S6, the clamping device Vb in the blood circuit is opened (S7) as illustrated in FIG. 7. Then, whether or not there is any change by a predetermined value or greater (any drop by a predetermined value or greater) in the pressure (the venous pressure) detected by the pressure-detecting device (β) from the pressure stored in the zero-value-acquiring step S2 is checked (S8). If there is a change by the predetermined value or greater, it is regarded that the negative pressure in the negative-pressure portion has been propagated normally to the blood circuit (the venous blood circuit 3) through the communicating line La. Hence, the process proceeds to a step S9, where it is determined that the test is passed (the connection of the communicating line La is appropriate, and the connection in the portion from the distal end of the venous blood circuit 3 to the blood pump 4 is appropriate with no blockage) (S9).

In contrast, if there is no change by the predetermined value or greater in the step S5, it cannot be regarded that the negative pressure in the negative-pressure portion has been propagated to the blood circuit (the arterial blood circuit 2) through the communicating line La. Hence, the process proceeds to a step S10, where it is determined that the test is failed (the communicating line La is not connected or the portion from the distal end of the arterial blood circuit 2 to the blood pump 4 has a blockage). If it is determined that the test is failed like this, the value detected by the pressure-detecting device (γ) is checked in a step S11. If there is no change from the pressure stored in zero-value-acquiring step S2, the process proceeds to a step S12, where it is determined that the arterial blood circuit 2 has a blockage. If the detected pressure is the atmospheric pressure, the process proceeds to a step S13, where it is determined that the communicating line La is not connected to the arterial blood circuit 2.

If there is no change by the predetermined value or greater in the step S8, it cannot be regarded that the negative pressure in the negative-pressure portion has been propagated to the blood circuit (the venous blood circuit 3) through the communicating line La. Hence, the process proceeds to a step S14, where it is determined that the test is failed (the communicating line La is not connected or the portion from the distal end of the venous blood circuit 3 to the blood pump 4 has a blockage). If it is determined that the test is failed like this, the value detected by the pressure-detecting device (γ) is checked in a step S15. If there is no change from the pressure stored zero-value-acquiring step S2, the process proceeds to a step S16, where it is determined that the venous blood circuit 3 has a blockage, if the detected pressure is the atmospheric pressure, the process proceeds to a step S17, where it is determined that the communicating line La is not connected to the venous blood circuit 3.

Now, changes in the pressures measured in the connection-checking test will be described with reference to the graph illustrated in FIG. 8.

When the pressurizing pump 9 is activated in the pressure-applying step S1, the pressure representing the dialysate pressure and detected by the pressure-detecting device (γ) drops, whereby a negative pressure is generated. When the electromagnetic valve V5 is opened at start time T1 for the zero-value-acquiring step S2, the pressure detected by the pressure-detecting device (γ) rises. Subsequently when the electromagnetic valve V11 is opened at start time T2 for the propagating step S3, the pressure detected by the pressure-detecting device (γ) further rises until time T3 when the clamping device Va of the arterial blood circuit 2 is opened. During the period from the stat of the pressure-applying step a1 to the time T3, the pressure detected by the pressure-detecting device (α) and the pressure detected by the pressure-detecting device (β) are constant.

When the clamping device Va is opened at the time T3 for the arterial propagating step S4, the pressure detected by the pressure-detecting device (γ) slightly rises, whereas the pressure detected by the pressure-detecting device α rapidly drops. Subsequently, when the clamping device Vb is opened at time T4 for the venous propagating step S7, the pressures detected by the pressure-detecting device α and the pressure-detecting device (γ) rapidly rise, whereas the pressure detected by the pressure-detecting device (β) slightly drops. During the period from the time T3 to the time T4, the pressure detected by the pressure-detecting device (β) is constant.

In the checking steps (S5, S8, S11, S15, and others in the present embodiment) of the connection-checking test, the value detected by the pressure-detecting device that shows a greater pressure change is selectively used. Hence, whether or not the connection of the communicating line La is appropriate and whether or not there is any blockage in the flow route of the blood circuit can be determined more smoothly and more accurately.

According to the present embodiment, the pressure applying step S1, the propagating step S3, and the checking steps (S5 and S8) are executed. Hence, whether or not the connection of the communicating line La is appropriate can be determined more accurately. Furthermore, in the checking steps according to the present embodiment, not only whether or not the connection of the communicating line La is appropriate but also whether or got there is any blockage in the flow route of the blood circuit can be checked. Hence, whether or not the connection of the communicating line La is appropriate and whether or not there is any blockage in the blood circuit can be determined accurately.

In the pressure-applying step S1, a negative pressure or a positive pressure is applied to the flow route of the tube section. In the propagating step S3, the negative pressure or the positive pressure is propagated to the flow route of the blood circuit through the communicating line La. Hence, regardless of the state of the blood circuit (for example, even in a state where the blood circuit is being inserted in the patient), whether or not the connection of the communicating line La is appropriate can be determined accurately. Moreover, in the pressure-applying step S1, a negative pressure is applied to the flow route of the tube section. Accordingly, the negative pressure generated in the tube section propagates to the blood circuit. Hence the occurrence of a situation where a positive pressure is propagated and the dialysate in the tube section accidentally flows into the blood circuit can be prevented.

In particular, the communicating line La according to the present embodiment is connectable to the dialysate drain line L2 in the tube section or to the connection port 14 provided to the branch line L10 branching off from the dialysate drain line L2. Hence, for example, during priming, the priming solution (the physiological saline solution or the like serving as a substitution solution) in the blood circuit can be drained into the dialysate drain line L2 or into the branch line L10 branching off therefrom. Furthermore, in the connection-checking test, whether or not the connection of the communicating line La is appropriate can be determined accurately.

Now, a blood purification apparatus according to a second embodiment of the present invention will be described.

As with the case of the first embodiment, the blood purification apparatus according to the present embodiment is used in blood purification treatment (hemodialysis treatment) in which blood of a patient can be purified while being extracorporeally circulated. As illustrated in FIG. 1, the apparatus includes a blood circuit including an arterial blood circuit 2 and a venous blood circuit 3 through which the blood of the patient is allowed to be extracorporeally circulated, a dialyzer 1 (a blood purification device) provided between the arterial blood circuit 2 and the venous blood circuit 3 and that purifies the blood flowing in the blood circuit, a tube section including a dialysate introduction line L1 and a dialysate drain line L2 provided in a dialysis-apparatus body 8, and a control device 16. Elements that are the same as those described in the first embodiment are denoted by corresponding ones of the reference numerals, and description of such elements is omitted.

Now, a specific control process executed in the connection-checking test by the control device 16 according to the second embodiment will be described with reference to the flow chart illustrated in FIG. 9.

First, as illustrated in FIG. 1, the wye tube a is connected to the distal ends of the arterial blood circuit 2 and the venous blood circuit 3, and the communicating line La is connected to the distal end of the wye tube a and to the connection port 14 (a state for performing priming). In the tube section, as illustrated in FIG. 3, the electromagnetic valves (V2, V3, V4, V5, V10, V11, and V8, or V12) are closed while the electromagnetic valves (V6 and V9) are opened. In this state, the pressurizing pump 9 is activated. Thus, a negative-pressure portion is formed in a predetermined part of the tube section (the pressure-applying step S1). Note that the clamping device Vc is kept dosed during the connection-checking test. The other electromagnetic valves (the electromagnetic valves V1, V7, and others) in the tube section and the electromagnetic valves and the clamping devices in the blood circuit may each be either opened or closed. During the connection checking step, the duplex pump 7 is kept stopped, and the relief valve VLa and the back-pressure valve VLb are closed.

Subsequently, as illustrated in FIG. 4, the electromagnetic valve V5 is opened, and the electromagnetic valve V9 is closed. Then, the pressures (the arterial pressure, the venous pressure, and the dialysate pressure) detected by the pressure-detecting devices (α, β, and γ) in this state are stored (a zero-value-acquiring step S2). Furthermore, as illustrated in FIG. 5, while the clamping devices (Va and Vb) in the blood circuit are closed, the electromagnetic valve V11 in the tube section is opened. Thus, the negative pressure in the negative-pressure portion formed in the pressure-applying step S1 is propagated to the blood circuit through the communicating line La (the propagating step S3). Note that in the propagating step S3, the clamping devices (Va and Vb) may be opened.

After the step S3, whether or not there is any change by a predetermined value or greater (any rise, by a predetermined value or greater) in the pressure (the dialysate pressure) detected by the pressure-detecting device (γ) from the pressure stored in the sero-value-acquiring step S2 is checked (S4). If there is a change by the predetermined value or greater, it is regarded that the negative pressure in the negative-pressure portion has been propagated normally to the blood circuit through the communicating line La. Hence, the process proceeds to a step S5, where it is determined that the test is passed (the connection of the communicating line La and the blood circuit are appropriate with no blockage). If the clamping device Va and the clamping device Vb are opened, in the step S4, whether or not there is any change by a predetermined value or greater (any drop, by a predetermined value or greater) in the pressure (the dialysate pressure) detected by the pressure-detecting device (α) (the arterial pressure) or the pressure-detecting device (β) (the venous pressure) from the pressure stored in the zero-value-acquiring step S2 may be checked.

In contrast, if there is no change by the predetermined value or greater in the step S4, it cannot be regarded that the negative pressure in the negative-pressure portion has been propagated to the blood circuit through the communicating line La. Hence, it is determined that the test is failed. If the pressure (the dialysate pressure) detected by the pressure-detecting device (γ) is the atmospheric pressure, it is determined that the communicating line La is not connected. Hence, it is determined that the test is failed (S6). If there is no change by the predetermined value or greater (no rise by the predetermined value or greater) in the pressure (the dialysate pressure) detected by the pressure-detecting device (γ) from the pressure stored sit zero-value-acquiring step S2, it is determined that the test is failed (S7) because the blood circuit has a blockage.

Now, a blood purification apparatus according to a third embodiment of the present invention will be described.

As with the case of the first embodiment, the blood purification apparatus according to the present embodiment is used in blood purification treatment (hemodialysis treatment) in which blood of a patient can be purified while being extracorporeally circulated. As illustrated in FIGS. 11 and 12, the apparatus includes a blood circuit including an arterial blood circuit 2 and a venous blood circuit 3 through which the blood of the patient is allowed to be extracorporeally circulated, a dialyzer 1 (a blood purification device) provided between the arterial blood circuit 2 and the venous blood circuit 3 and that purifies the blood flowing in the blood circuit, a tube section including a dialysate introduction line L1 and a dialysate drain line L2 provided in a dialysis-apparatus body B, and a control device 16. Elements that are the same as those described in the first embodiment are denoted by corresponding ones of the reference numerals, and description of such elements is omitted.

In the blood purification apparatus according to the present embodiment, an overflow line Lb extends between the top of the air-trap chamber 6 and the connection port 14. The overflow line Lb is provided with a clamping device Vd for opening and closing the flow route. The overflow line Lb serves as a communicating line that is connected to the tube section in the dialysis-apparatus body B and to the blood circuit, thereby allowing the flow route in the tube section and the flow route in the blood circuit to communicate with each other. In the present embodiment, when priming is performed, the distal ends of the arterial blood circuit 2 and the venous blood circuit 3 are connected to each other to form a closed circuit. Thus, the physiological saline solution (the substitution solution) supplied from the storage bag b is allowed to be supplied and filled into the blood circuit, and an overflowed portion of the physiological saline solution is allowed to be drained into the dialysate drain line L2 through the overflow line Lb.

Now, a specific control process executed in the connection-checking test by the control device 6 according to the third embodiment will be described with reference to the flow chart illustrated in FIG. 10.

First, as illustrated in FIG. 11, the distal ends of the arterial blood circuit 2 and the venous blood circuit 3 are connected to each other to form a closed circuit, and the overflow line Lb extending from the top of the air-trap chamber 6 is connected to the connection port 14 (a state for performing priming). Subsequently, as illustrated in the drawing, the electromagnetic valves (V2, V3, V4, V5, V6, and V11) in the tube;section and the clamping device Vd are closed while the electromagnetic valve V10 is opened. In this state, the ultrafiltration pump 8 is activated (the pressurizing pump 9 is kept stopped) Thus, a negative-pressure portion is formed in a predetermined part of the tube section (a pressure-applying step S1). In the pressure-applying step S1, the pressures (the arterial pressure, the venous pressure, and the dialysate pressure) detected by the respective pressure-detecting devices (($\alpha$), ($\beta$), and ($\gamma$)) are stored. Note that the clamping device Vc is kept closed during the connection-checking test. The other electromagnetic valves in the tube section and the electromagnetic valves and the clamping devices the blood circuit may each be either opened or closed. During the connection-checking step, the duplex pump 7 is kept stopped, and the relief valve VLa and the back-pressure valve VLb are closed.

Subsequently, in a step S2, whether or not there is any change by a predetermined value or greater (any drop by a predetermined value or greater) in the pressure (the dialysate pressure) detected by the pressure-detecting device ($\gamma$) from the pressure stored in the pressure-applying step S1 is checked (S2). If there is a change by the predetermined value or greater, the process proceeds to a step S3, where it is determined that the test is passed. In contrast, if there is no change by the predetermined value or greater and if the pressure (the dialysate pressure) detected by the pressure-detecting device $\gamma$ is the atmospheric pressure, it is determined that the test is failed (S7) because the overflow line Lb is not connected to the connection port 14. If there is no change by the predetermined value greater (no drop by the predetermined value or greater) in the pressure (the dialysate pressure) detected by the pressure-detecting device ($\gamma$) from the pressure stored in the pressure-applying step S1, it is determined that the test is failed (S8) because the overflow line Lb is not connected to the clamping device Vd (an overflow clamp) or the clamping device Vd has a failure.

After the step S3, as illustrated in FIG. 12, the clamping device Vd and the clamping devices (Va and Vb) in the blood circuit are opened while the electromagnetic valve V1 in the tube section is closed. Thus, the negative pressure in the negative-pressure portion formed in the pressure-applying step S1 is propagated to the blood circuit through the overflow line Lb (a propagating step S4). Then, whether or not there is any change by a predetermined value or greater (any rise by a predetermined value or greater) in the pressure (the dialysate pressure) detected by the pressure-detecting device ($\gamma$) from the pressure stored in the pressure-applying step S1 is checked (S5). If there is a change by the predetermined value or greater, the process proceeds to step S6, where it is determined that the test is passed.

In contrast, if there is no change by the predetermined value or greater in the step S5 and if there is no change by the predetermined value or greater (no rise by the predetermined value or greater) in the pressure (the dialysate pressure) detected by the pressure-detecting device ($\gamma$) from the pressure stored in the pressure-applying step S1, it is determined that the test is failed (S9) because an end of the clamping device Vd (an overflow clamp) is closed or has a failure. If the detected pressure is the atmospheric pressure, it is determined that the test is failed (S10) because the blood circuit has an unconnected part.

Now, a blood purification apparatus according to a fourth embodiment of the present invention will be described.

As with the case of the first embodiment, the blood purification apparatus according to the present embodiment is used in blood purification treatment (hemodialysis treatment) in which blood of a patient can be purified while being extracorporeally circulated. As illustrated in FIG. 1, the apparatus includes a blood circuit including an arterial blood circuit 2 and a venous blood circuit 3 through which the blood of the patient is allowed to be extracorporeally circulated, a dialyzer 1 (a blood purification device) provided between the arterial blood circuit 2 and the venous blood circuit 3 and that purifies the blood flowing in the blood circuit, a tube section including a dialysate introduction line L1 and a dialysate drain line L2 provided in a dialysis-apparatus body B, and a control device 16. Elements that are the same as those described in the first embodiment are denoted by corresponding ones of the reference numerals, and description of such elements is omitted.

Now, a specific control process executed in the connection-checking test by the control device 16 according to the fourth embodiment will be described with reference to the flow chart illustrated in FIG. 13.

First, as illustrated in FIG. 1, the wye tube (a) is connected to the distal ends of the arterial blood circuit 2 and the venous blood circuit 3, and the communicating line La, is connected to the distal end of the wye tube a and to the connection port 14 (a state for performing priming). In the tube section, as illustrated in FIG. 14, the electromagnetic valves (V2, V3, V4, V9, V10, and V11) are closed while the electromagnetic valves (V5, V8, and V12) are opened. In this state a liquid-supplying pressure (a liquid pressure of the dialysate supplied into the dialysate introduction line L1) is applied (with the pressurizing pump 9 kept stopped). Thus, a positive-pressure portion is formed in a predetermined part of the tube section (the pressure-applying step S1). In this step, the pressures (the arterial pressure, the venous pressure, and the dialysate pressure) detected by the pressure-detecting devices (($\alpha$), ($\beta$), and ($\gamma$)) are stored. Note that the clamping device Vc is kept closed during the connection-checking test. The other electromagnetic valves in the tube section and the electromagnetic valves and the clamping devices in the blood circuit may each be either opened or closed. During the connection-checking test, the duplex pump 7 is kept stopped, and the relief valve VLa and the back-pressure valve VLb are closed.

Subsequently, a illustrated in FIG. 15, the electromagnetic valve V10 is opened. Furthermore, in the blood circuit, the clamping device Va is closed while the clamping device Vb is open. Thus, the positive pressure in the positive-pressure portion formed in the pressure-applying step S1 is propagated to the blood circuit through the communicating line La (a propagating step S2). In the propagating step S2, the clamping device Va may be opened while the clamping device Vb may be closed, or the clamping device Va and Vb) may be opened.

After the step S2, whether or not there is any change by a predetermined value or greater (any drop by a predetermined value or greater) in the pressure (the dialysate pressure) detected by the pressure-detecting device ($\gamma$) from the pressure stored in the pressure-applying step S1 is checked (S3). If there is a change by the predetermined value or greater, it is regarded that the positive pressure in the positive-pressure portion has been propagated normally to the blood circuit through the communicating line La. Hence, the process proceeds to a step S4, where it is determined that the test is passed (the connection of the communicating line La and the blood circuit are appropriate with no blockage).

In contrast, if there is no change by the predetermined value or greater in the step S3, it cannot be regarded that the positive pressure in the positive-pressure portion has been propagated to the blood circuit through the communicating line La. Hence, it is determined that the test is failed. If there is no change by the predetermined value or greater (no drop by the predetermined value or greater) in the pressure (the dialysate pressure) detected by the pressure-detecting device (γ) from the pressure stored in the pressure-applying step S1, it is determined that the test is failed (S5) because the blood circuit has a blockage. If the pressure (the dialysate pressure) detected by the pressure-detecting device (γ) is the atmospheric pressure, it is determined that the test is failed (S6) because the communicating line La is not connected.

Now, a blood purification apparatus according to a fifth embodiment of the present invention will be described.

As with the case of the first embodiment, the blood purification apparatus according to the present embodiment is used in blood purification treatment (hemodialysis treatment) in which blood of a patient can be purified while being extracorporeally circulated. As illustrated in FIGS. 17 to 20, the apparatus includes a blood circuit including an arterial blood circuit 2 and a venous blood circuit 3 through which the blood of the patient is allowed to be extracorporeally circulated, a dialyzer 1 (a blood purification device) provided between the arterial blood circuit 2 and the venous blood circuit 3 and that purifies the blood flowing in the blood circuit, a tube section including a dialysate introduction line L1 and a dialysate drain line L2 provided in a dialysis-apparatus body B, and a control device 16. Elements that are the same as those described in the first embodiment are denoted by corresponding ones of the reference numerals and description of such elements is omitted.

In the blood purification apparatus according to the present embodiment, a liquid-level-adjusting line L11 provided with a liquid-level-adjusting pump 17 and an electromagnetic valve V14 extends from the top of the air-trap chamber 6. When the liquid-level-adjusting pump 17 is activated to undergo normal rotation while the electromagnetic valve V14 is open, air in the air-trap chamber 6 is discharged to the outside and the liquid surface is raised. When the liquid-level-adjusting pump 17 is activated to undergo reverse rotation, air is introduced into the air-trap chamber 6 and the liquid surface is lowered.

Now, a specific control process executed in the connection-checking test by the control device 16 according to the fifth embodiment will be described with reference to the flow chart illustrated in FIG. 16.

First, as illustrated in FIG. 17, the wye tube (a) is connected to the distal ends of the arterial blood circuit 2 and the venous blood circuit 3, and the communicating line La is connected to the distal end of the wye tube (a) and to the connection port 14 (a state for performing priming). In the tube section, as illustrated in the drawing, the electromagnetic valves (V1 and V2) are dosed. Furthermore, in the blood circuit, the clamping devices (Va and Vb) are closed while the electromagnetic valve V14 is opened. In this state, the liquid-level-adjusting pump 17 is activated to undergo normal rotation. Thus, a negative-pressure portion is formed in a part represented by dotted lines in the drawing (the pressure-applying step S1). In the pressure-applying step S1, the pressure (the arterial pressure) detected by the pressure-detecting device (α) and the pressure (the venous ores detected by the pressure-detecting device (β) are stored. Note that the clamping device Vc is kept dosed during the connection-checking test. The other electromagnetic valves in the tube section and the electromagnetic valves and the clamping devices in the blood circuit may each be either opened or closed. During the connection-checking step, the duplex pump 7 is kept stopped, and the relief valve VLa and the back-pressure valve VLb are closed.

Subsequently, as illustrated in FIG. 1, while the clamping device Va is kept closed, the clamping device Vb is opened (that is, the clamping device Va is closed and the clamping device Vb is open) and the electromagnetic valve V14 and the electromagnetic valves (V10 and V11) in the tube section are closed. Thus, the negative pressure in the negative-pressure portion formed in the pressure-applying step S1 is propagated to the tube section of the dialysis-apparatus body B through the communicating line La (a propagating step S2). Then, whether or not there is any change by a predetermined value or greater (any rise by a predetermined value or greater) in the pressure (the venous pressure) detected by the pressure-detecting device (β) from the pressure stored in the pressure-applying step S1 is checked (S3). If there is a change by the predetermined value or greater, it is regarded that the negative pressure in the negative-pressure portion of the venous blood circuit 3 is normally propagated to the tube section through the communicating line La. Hence, the process proceeds to a step S4, where it is determined that the test is passed (the venous blood circuit 3 is appropriately connected to the communicating line La).

Subsequently, as illustrated in FIG. 19, while the clamping device Va is opened (that is, in a state where the clamping device Va and the clamping device Vb are both open), the electromagnetic valves (V14, V10, and V11) are kept closed. Thus, the negative pressure is kept propagated through the communicating line La (a propagating step S5). Then, whether or not there is any change by a predetermined value or greater (any rise by a predetermined value or greater) in the pressure (the arterial pressure) detected by the pressure-detecting device α from the pressure stored in the pressure-applying step S1 is checked (S6). If there is a change by the predetermined value or greater, it is regarded that the negative pressure in the negative-pressure portion of the arterial blood circuit 2 is normally propagated to the tube section through the communicating line La. Hence, the process proceeds to a step S7, where it is determined that the test is passed (the arterial blood circuit 2 is appropriately connected to the communicating lane La).

After the step S7, as illustrated in FIG. 20, the electromagnetic valve V12 is closed and the electromagnetic valve V11 is opened (with the electromagnetic valve V9 kept open) in the tube section in a step S8. Then, in a step S9, whether or not there is any change by a predetermined value or greater in the pressure (the venous pressure) detected by the pressure-detecting device β from the pressure stored in the pressure-applying step S1 is checked. If the pressure (the venous pressure) detected by the pressure-detecting device (β) is the atmospheric pressure, the process proceeds to a step S10, where it is determined that the test is passed. If there is no change, it is determined that the test is failed (S11) because the communicating line La has a blockage.

In contrast, if the pressure (the venous pressure) detected by the pressure-detecting device (β) in the step S3 has risen up to the atmospheric pressure, it is determined that the test is failed (S12) because the venous blood circuit 3 is not connected to the communicating line La. If there is no change, it is determined that the test is failed (S13) because the clamping device Vb (a venous clamp) has a failure. If the pressure (the arterial pressure) detected by the pressure-detecting device (α) in the step S6 has risen up to the atmospheric pressure, it is determined that the test is failed (S14) because the arterial blood circuit 2 is not connected to the communicating line La. If there is no change, it is determined that the test is failed (S15) because the arterial blood circuit 2 has a blockage.

In the above case, a negative pressure is applied to the flow route of the blood circuit in the pressure-applying step S1. Alternatively a positive pressure may be applied to the flow route. According to the present embodiment, in the pressure-applying step S1, a negative pressure or a positive pressure is applied to the flow route of the blood circuit. Furthermore, in the propagating step S2, the negative pressure or the positive pressure is propagated to the flow route of the tube section through the communicating line La. Hence, regardless of the state of the tube section, whether or not the connection of the communicating line is appropriate can be determined accurately.

While some embodiments have been described above, the present invention is not limited thereto. For example, a connection-checking test may be performed on a communicating line whose end is connected to the collecting port 10 or to any other part (such as the detour line L5) of the tube section. Moreover, the devices such as the device that applies a negative pressure or a positive pressure in the pressure-applying step, and the device that checks whether or not the negative pressure or the positive pressure has been propagated in the propagating step may each be any other device excluding the pressurizing pump 9 and the liquid-level-adjusting pump 17. The blood purification apparatus to which any of the above embodiments is applied may be in any form. For example, the apparatus may be configured such that the dialysate is introduced into and drained from a chamber in replacement of the duplex pump 7. Moreover, the apparatus may include a blood purification device of another form in replacement of the dialyzer 1.

The present invention is also applicable to any blood purification apparatus having another external shape, another additional function, and so forth, as long as the apparatus is capable of executing a pressure-applying step in which a negative pressure or a positive pressure is applied to the flow route of one of a tube section and a blood circuit; a propagating step in which the negative pressure or the positive pressure applied in the pressure-applying step is propagated to the flow route of the other of the tube section and the blood circuit through a communicating line; and a checking step in which whether or not the propagation of the negative pressure or the positive pressure in the propagating step is successful is checked with reference to the pressures detected by the pressure-detecting devices, and in which whether or not the connection of the communicating line is appropriate is checked with reference to whether or not the propagation of the negative pressure or the positive pressure is successful.

REFERENCE SIGN LIST

1 dialyzer (blood purification device)
2 arterial blood circuit
3 venous blood circuit
4 blood pump
5, 6 air-trap chamber
7 duplex pump
8 ultrafiltration pump
9 pressurizing pump
10 collecting port
11, 12 filter
13 degassing chamber
14 connection port
15 chamber
16 control device
L1 dialysate introduction line
L2 dialysate drain line
L3, L4, L5, L6 detour line
L7, L8, L9 bypass line
L10 branch line
La communicating line
Lb overflow line
Lc supply line
$\alpha$, $\beta$, $\gamma$ pressure-detecting device

The invention claimed is:

1. A blood purification apparatus comprising:
a blood circuit including an arterial blood circuit and a venous blood circuit through which blood of a patient is allowed to be extracorporeally circulated;
a blood purification device provided between the arterial blood circuit and the venous blood circuit and that purifies the blood flowing in the blood circuit;
a tube section including a dialysate introduction line and a dialysate drain line through which dialysate is introduced into and drained from the blood purification device, respectively;
a branch line provided between and connecting the dialysate introduction line and the dialysate drain line of the tube section,
a first pressure-detecting device located in the venous blood circuit, a second pressure-detecting device located in the arterial blood circuit, and a third pressure-detecting device located in the tube section, wherein the first and second pressure-detecting devices detects a pressure in the blood circuit and the third pressure-detecting device detects a pressure in the tube section;
a communicating line connected to the tube section and to the blood circuit and that allows a flow route of the tube section and a flow route of the blood circuit to communicate with each other; and
a control device that controls opening and closing of any clamping devices included in the tube section or in the blood circuit and operation of any pumps included in the tube section or in the blood circuit,
wherein the control device that performs the controlling, executes
a pressure-applying step in which a negative pressure or a positive pressure is applied to the flow route of one of the tube section and the blood circuit by one of the pumps;
a propagating step in which the negative pressure or the positive pressure applied in the pressure-applying step is propagated to the flow route of an other of the tube section and the blood circuit through the communicating line; and
a checking step in which whether or not the propagation of the negative pressure or the positive pressure in the propagating step is successful is checked with reference to the pressure detected by the first, second, or third pressure-detecting device and in which whether or not the connection of the communicating line is appropriate is checked with reference to whether or not the propagation of the negative pressure or the positive pressure is successful.

2. The blood purification apparatus according to claim 1, wherein not only whether or not the connection of the communicating line is appropriate but also whether or not the flow route of the blood circuit has any blockage is checked in the checking step.

3. The blood purification apparatus according to claim 1, wherein the negative pressure or the positive pressure is applied to the flow route of the tube section in the pressure-applying step, and the negative pressure or the positive pressure is propagated to the flow route of the blood circuit through the communicating line in the propagating step.

4. The blood purification apparatus according to claim 3, wherein the negative pressure is applied to the flow route of the tube section in the pressure-applying step.

5. The blood purification apparatus according to claim 1, wherein the negative pressure or the positive pressure is applied to the flow route of the blood circuit in the pressure-applying step, and the negative pressure or the positive pressure is propagated to the flow route of the tube section through the communicating line in the propagating step.

6. The blood purification apparatus according to claim 1, wherein the communicating line is connectable to a connection port provided to the dialysate drain line or to the branch line branching off from the dialysate drain line in the tube section.

7. The blood purification apparatus according to claim 1, wherein the second pressure-detecting device is located on an upstream side of a blood pump.

8. The blood purification apparatus according to claim 7, wherein the second pressure-detecting device is located between the blood pump and a clamping device.

9. The blood purification apparatus according to claim 1, wherein the pumps are pressurizing pumps or liquid-level-adjusting pumps.

10. The blood purification apparatus according to claim 9, wherein the venous blood circuit includes an air-trap chamber and the air trap chamber is provided with the first pressure-detecting device.

11. The blood purification apparatus according to claim 10, wherein the second pressure-detecting device is located on an upstream side of a blood pump.

12. The blood purification apparatus according to claim 1, wherein the third pressure-detecting device is located within the dialysate drain line.

13. The blood purification apparatus according to claim 12, wherein the third pressure-detecting device is located on a downstream side of an electromagnetic valve.

14. The blood purification apparatus according to claim 13, wherein the third pressure-detecting device is located between a first bypass line and a second bypass line.

15. The blood purification apparatus according to claim 1, wherein a relief valve is located within a detour line that is connected to the dialysate drain line.

16. The blood purification apparatus according to claim 15, wherein the detour line is connected on an upstream side of a duplex pump and a downstream side of the duplex pump so that the duplex pump is capable of being bypassed by the detour line.

17. The blood purification apparatus according to claim 1, wherein a detour line has a first end connected to the dialysate drain line and a second end connected to the dialysate drain line, and a first end of the branch line is connected to the detour line.

18. The blood purification apparatus according to claim 17, wherein a second detour line extends between the dialysate introduction line and the dialysate drain line and a second end of the branch line is connected to the second detour line.

19. The blood purification apparatus according to claim 18, wherein the second detour line includes an electromagnetic valve and the electromagnetic valve is located on a downstream side of the branch line.

20. The blood purification apparatus according to claim 1, wherein one end of the communicating line is connected to the branch line.

* * * * *